(12) United States Patent
Spitler

(10) Patent No.: US 11,925,776 B2
(45) Date of Patent: Mar. 12, 2024

(54) SECUREMENT DEVICE

(71) Applicant: C. R. Bard, Inc., Franklin Lakes, NJ (US)

(72) Inventor: James Spitler, Orlando, FL (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 197 days.

(21) Appl. No.: 17/335,974

(22) Filed: Jun. 1, 2021

(65) Prior Publication Data

US 2021/0283375 A1 Sep. 16, 2021

Related U.S. Application Data

(63) Continuation of application No. 13/813,102, filed as application No. PCT/US2010/044016 on Jul. 30, 2010, now Pat. No. 11,020,565.

(51) Int. Cl.
*A61M 25/02* (2006.01)

(52) U.S. Cl.
CPC ....... *A61M 25/02* (2013.01); *A61M 2025/024* (2013.01); *A61M 2025/0266* (2013.01); *A61M 2025/028* (2013.01)

(58) Field of Classification Search
CPC ............ A61M 25/02; A61M 2025/024; A61M 2025/028; A61M 2025/0266
See application file for complete search history.

(56) References Cited

U.S. PATENT DOCUMENTS

| 2,525,398 A | 10/1950 | Collins |
| 2,533,961 A | 12/1950 | Rousseau et al. |
| 2,707,953 A | 5/1955 | Ryan |
| 3,046,984 A | 7/1962 | Eby |
| 3,059,645 A | 10/1962 | Hasbrouck et al. |
| 3,064,648 A | 11/1962 | Bujan |
| 3,167,072 A | 1/1965 | Stone et al. |
| 3,194,235 A | 7/1965 | Cooke |
| 3,288,137 A | 11/1966 | Lund |
| 3,482,569 A | 12/1969 | Raaelli, Sr. |
| 3,602,227 A | 8/1971 | Andrew |
| 3,613,663 A | 10/1971 | Johnson |

(Continued)

FOREIGN PATENT DOCUMENTS

| CA | 1311977 C | 12/1992 |
| CA | 1318824 C | 6/1993 |

(Continued)

OTHER PUBLICATIONS

CA 2,737,640 filed Sep. 18, 2012 First Office Action dated Sep. 24, 2015.

(Continued)

*Primary Examiner* — Emily L Schmidt

(74) *Attorney, Agent, or Firm* — Rutan & Tucker LLP

(57) ABSTRACT

A securement device holds a medical article having flexible portions in position upon the body of a patient and inhibits movement of the medical article. The medical article may be insertable into the securement device from above from below or along a longitudinal axis of the device. The securement device may have abutment surfaces which interact with the flexible portions of the medical article to further inhibit rotation of the device. A securement kit can include a securement device and a catheter.

9 Claims, 44 Drawing Sheets

(56) References Cited

U.S. PATENT DOCUMENTS

| | | |
|---|---|---|
| 3,630,195 A | 12/1971 | Santomieri |
| 3,677,250 A | 7/1972 | Thomas |
| 3,766,915 A | 10/1973 | Rychlik |
| 3,782,383 A | 1/1974 | Thompson et al. |
| 3,826,254 A | 7/1974 | Mellor |
| 3,834,380 A | 9/1974 | Boyd |
| 3,856,020 A | 12/1974 | Kovac |
| 3,863,527 A | 2/1975 | Berning |
| 3,896,527 A | 7/1975 | Miller et al. |
| 3,900,026 A | 8/1975 | Wagner |
| 3,901,226 A | 8/1975 | Scardenzan |
| 3,906,946 A | 9/1975 | Nordstrom |
| 3,973,565 A | 8/1976 | Steer |
| 4,020,835 A | 5/1977 | Nordstrom et al. |
| 4,057,066 A | 11/1977 | Taylor |
| 4,059,105 A | 11/1977 | Cutruzzula et al. |
| 4,082,094 A | 4/1978 | Dailey |
| 4,129,128 A | 12/1978 | McFarlane |
| 4,142,527 A | 3/1979 | Garcia |
| 4,161,177 A | 7/1979 | Fuchs |
| 4,165,748 A | 8/1979 | Johnson |
| D252,822 S | 9/1979 | McFarlane |
| 4,193,174 A | 3/1980 | Stephens |
| 4,224,937 A * | 9/1980 | Gordon ............... A61M 25/02 128/DIG. 26 |
| 4,248,229 A | 2/1981 | Miller |
| 4,250,880 A | 2/1981 | Gordon |
| 4,275,143 A | 6/1981 | Sakurai |
| 4,275,721 A | 6/1981 | Olson |
| 4,284,076 A | 8/1981 | Hall |
| 4,316,461 A | 2/1982 | Marais et al. |
| 4,326,519 A | 4/1982 | D'Alo et al. |
| 4,333,468 A | 6/1982 | Geist |
| 4,362,156 A | 12/1982 | Feller, Jr. et al. |
| 4,392,853 A | 7/1983 | Muto |
| 4,397,647 A | 8/1983 | Gordon |
| 4,449,975 A | 5/1984 | Perry |
| 4,453,933 A | 6/1984 | Speaker |
| 4,470,410 A | 9/1984 | Elliott |
| 4,480,639 A | 11/1984 | Peterson et al. |
| 4,484,913 A | 11/1984 | Swauger |
| 4,516,968 A | 5/1985 | Marshall et al. |
| 4,517,971 A | 5/1985 | Sorbonne |
| 4,563,177 A | 1/1986 | Kamen |
| 4,585,443 A | 4/1986 | Kaufman |
| 4,627,842 A | 12/1986 | Katz |
| 4,632,670 A | 12/1986 | Mueller, Jr. |
| 4,633,863 A | 1/1987 | Filips et al. |
| 4,645,492 A | 2/1987 | Weeks |
| 4,669,458 A | 6/1987 | Abraham et al. |
| 4,683,882 A | 8/1987 | Laird |
| 4,699,616 A | 10/1987 | Nowak et al. |
| 4,711,636 A | 12/1987 | Bierman |
| 4,737,143 A | 4/1988 | Russell |
| 4,742,824 A | 5/1988 | Payton et al. |
| 4,792,163 A | 12/1988 | Kulle |
| 4,808,162 A | 2/1989 | Oliver |
| 4,822,342 A | 4/1989 | Brawner |
| 4,826,486 A | 5/1989 | Palsrok et al. |
| 4,832,019 A | 5/1989 | Weinstein et al. |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,897,082 A | 1/1990 | Erskine |
| 4,898,587 A | 2/1990 | Mera |
| 4,919,654 A | 4/1990 | Kalt |
| 4,921,199 A | 5/1990 | Villaveces |
| 4,955,864 A | 9/1990 | Hajduch |
| 4,976,698 A | 12/1990 | Stokley |
| 4,976,700 A | 12/1990 | Tollini |
| 4,981,475 A | 1/1991 | Haindl |
| 4,986,815 A | 1/1991 | Schneider |
| 4,997,421 A | 3/1991 | Palsrok et al. |
| 5,037,397 A | 8/1991 | Kalt et al. |
| 5,069,206 A | 12/1991 | Crosbie |
| 5,073,170 A | 12/1991 | Schneider |
| 5,074,847 A | 12/1991 | Greenwell et al. |
| 5,084,026 A | 1/1992 | Shapiro |
| 5,098,399 A | 3/1992 | Tollini |
| 5,112,313 A | 5/1992 | Sallee |
| 5,116,324 A | 5/1992 | Brierley et al. |
| 5,137,519 A | 8/1992 | Littrell et al. |
| 5,147,322 A | 9/1992 | Bowen et al. |
| 5,156,641 A | 10/1992 | White |
| 5,167,630 A | 12/1992 | Paul |
| 5,192,273 A | 3/1993 | Bierman |
| 5,192,274 A | 3/1993 | Bierman |
| 5,195,981 A | 3/1993 | Johnson |
| 5,215,532 A | 6/1993 | Atkinson |
| 5,236,421 A | 8/1993 | Becher |
| 5,238,010 A | 8/1993 | Grabenkort et al. |
| 5,266,401 A | 11/1993 | Tollini |
| 5,267,967 A | 12/1993 | Schneider |
| 5,290,248 A | 3/1994 | Bierman et al. |
| 5,292,312 A | 3/1994 | Delk et al. |
| 5,304,146 A | 4/1994 | Johnson et al. |
| 5,306,243 A | 4/1994 | Bonaldo |
| D347,060 S | 5/1994 | Bierman |
| 5,314,411 A | 5/1994 | Bierman et al. |
| 5,322,097 A | 6/1994 | Wright |
| 5,328,487 A | 7/1994 | Starchevich |
| 5,338,308 A | 8/1994 | Wilk |
| 5,342,317 A | 8/1994 | Claywell |
| 5,344,406 A | 9/1994 | Spooner |
| 5,352,211 A | 10/1994 | Merskelly |
| 5,354,282 A | 10/1994 | Bierman |
| 5,356,391 A | 10/1994 | Stewart |
| 5,370,627 A | 12/1994 | Conway |
| 5,372,589 A | 12/1994 | Davis |
| 5,380,293 A | 1/1995 | Grant |
| 5,380,395 A | 1/1995 | Uchida |
| 5,382,239 A | 1/1995 | Orr et al. |
| 5,395,344 A | 3/1995 | Beisang, III et al. |
| 5,402,776 A | 4/1995 | Islava |
| 5,403,285 A | 4/1995 | Roberts |
| 5,413,120 A | 5/1995 | Grant |
| 5,413,562 A | 5/1995 | Swauger |
| D359,120 S | 6/1995 | Sallee et al. |
| 5,443,460 A | 8/1995 | Miklusek |
| 5,456,671 A | 10/1995 | Bierman |
| 5,468,231 A | 11/1995 | Newman et al. |
| 5,470,321 A | 11/1995 | Forster et al. |
| D364,922 S | 12/1995 | Bierman |
| 5,480,719 A | 1/1996 | Tollini |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,527,293 A | 6/1996 | Zamierowski |
| 5,549,567 A | 8/1996 | Wolman |
| D375,355 S | 11/1996 | Bierman |
| D375,356 S | 11/1996 | Bierman |
| 5,577,516 A | 11/1996 | Schaeffer |
| 5,578,013 A | 11/1996 | Bierman |
| 5,593,395 A | 1/1997 | Martz |
| D377,831 S | 2/1997 | Bierman |
| 5,605,546 A | 2/1997 | Wolzinger et al. |
| 5,637,098 A | 6/1997 | Bierman |
| 5,664,581 A | 9/1997 | Ashley |
| 5,681,290 A | 10/1997 | Alexander |
| 5,685,859 A | 11/1997 | Kornerup |
| 5,686,096 A | 11/1997 | Khan et al. |
| 5,690,616 A | 11/1997 | Mogg |
| 5,693,032 A | 12/1997 | Bierman |
| 5,702,371 A | 12/1997 | Bierman |
| 5,722,959 A | 3/1998 | Bierman |
| 5,728,053 A | 3/1998 | Calvert |
| 5,755,225 A | 5/1998 | Hutson |
| 5,800,402 A | 9/1998 | Bierman |
| 5,800,410 A | 9/1998 | Gawreluk |
| 5,810,781 A | 9/1998 | Bierman |
| D399,954 S | 10/1998 | Bierman |
| 5,827,230 A | 10/1998 | Bierman |

(56) References Cited

U.S. PATENT DOCUMENTS

| | | |
|---|---|---|
| 5,827,239 A | 10/1998 | Dillon et al. |
| 5,833,666 A | 11/1998 | Davis et al. |
| 5,833,667 A | 11/1998 | Bierman |
| 5,855,591 A | 1/1999 | Bierman |
| 5,885,254 A | 3/1999 | Matyas |
| 5,897,519 A | 4/1999 | Shesol et al. |
| 5,911,707 A | 6/1999 | Wolvek et al. |
| 5,916,200 A | 6/1999 | Eppley et al. |
| 5,947,931 A | 9/1999 | Bierman |
| 6,050,934 A | 4/2000 | Mikhail et al. |
| D425,619 S | 5/2000 | Bierman |
| 6,067,985 A | 5/2000 | Islava |
| 6,099,509 A | 8/2000 | Brown, Jr. et al. |
| 6,113,577 A | 9/2000 | Hakky et al. |
| 6,132,398 A | 10/2000 | Bierman |
| 6,132,399 A | 10/2000 | Shultz |
| 6,213,979 B1 | 4/2001 | Bierman |
| 6,224,571 B1 | 5/2001 | Bierman |
| 6,228,064 B1 | 5/2001 | Abita et al. |
| 6,231,547 B1 | 5/2001 | O'Hara |
| 6,231,548 B1 | 5/2001 | Bassett |
| 6,258,066 B1 | 7/2001 | Urich |
| 6,283,945 B1 | 9/2001 | Bierman |
| 6,287,281 B1 | 9/2001 | Nishtala et al. |
| 6,290,676 B1 | 9/2001 | Bierman |
| 6,361,523 B1 | 3/2002 | Bierman |
| 6,375,639 B1 | 4/2002 | Duplessie et al. |
| 6,413,240 B1 | 7/2002 | Bierman et al. |
| 6,428,515 B1 | 8/2002 | Bierman et al. |
| 6,428,516 B1 | 8/2002 | Bierman |
| 6,436,073 B1 | 8/2002 | Von Teichert |
| 6,447,485 B2 | 9/2002 | Bierman |
| 6,447,486 B1 | 9/2002 | Tollini |
| 6,471,676 B1 | 10/2002 | DeLegge et al. |
| 6,482,183 B1 | 11/2002 | Pausch et al. |
| 6,488,664 B1 | 12/2002 | Solomon et al. |
| 6,491,664 B2 | 12/2002 | Bierman |
| 6,500,154 B1 | 12/2002 | Hakky et al. |
| D469,530 S | 1/2003 | Gomez |
| D470,936 S | 2/2003 | Bierman |
| 6,517,522 B1 | 2/2003 | Bell et al. |
| 6,551,285 B1 | 4/2003 | Bierman |
| 6,572,588 B1 | 6/2003 | Bierman et al. |
| 6,582,403 B1 | 6/2003 | Bierman et al. |
| 6,616,635 B1 | 9/2003 | Bell et al. |
| 6,626,890 B2 | 9/2003 | Nguyen et al. |
| 6,652,487 B1 | 11/2003 | Cook |
| 6,663,600 B2 | 12/2003 | Bierman et al. |
| 6,689,104 B2 | 2/2004 | Bierman |
| D492,411 S | 6/2004 | Bierman |
| 6,770,055 B2 | 8/2004 | Bierman et al. |
| 6,786,892 B2 | 9/2004 | Bierman |
| 6,809,230 B2 | 10/2004 | Hancock et al. |
| 6,827,705 B2 | 12/2004 | Bierman |
| 6,827,706 B2 | 12/2004 | Tollini |
| 6,827,707 B2 | 12/2004 | Wright et al. |
| 6,834,652 B2 | 12/2004 | Altman |
| 6,837,875 B1 | 1/2005 | Bierman |
| 6,866,652 B2 | 3/2005 | Bierman |
| D503,977 S | 4/2005 | Bierman |
| 6,951,550 B2 | 10/2005 | Bierman |
| 6,972,003 B2 | 12/2005 | Bierman et al. |
| 6,979,320 B2 | 12/2005 | Bierman |
| 6,981,969 B2 | 1/2006 | Chavez et al. |
| 7,014,627 B2 | 3/2006 | Bierman |
| 7,018,362 B2 | 3/2006 | Bierman et al. |
| 7,070,580 B2 | 7/2006 | Nielsen |
| 7,090,660 B2 | 8/2006 | Roberts et al. |
| D528,206 S | 9/2006 | Bierman |
| 7,153,291 B2 | 12/2006 | Bierman |
| 7,354,421 B2 | 4/2008 | Bierman |
| 7,377,472 B2 | 5/2008 | Brown et al. |
| 7,413,561 B2 | 8/2008 | Raulerson et al. |
| 7,799,001 B2 | 9/2010 | Bierman |
| 8,251,956 B2 | 8/2012 | Bierman et al. |
| 8,357,124 B2 | 1/2013 | Bierman |
| 8,734,400 B2 | 5/2014 | Ciccone |
| 8,740,852 B2 | 6/2014 | Aviles |
| 9,415,191 B2 | 8/2016 | Aviles |
| 9,561,348 B2 | 2/2017 | Bierman |
| 10,589,067 B2 | 3/2020 | Ciccone |
| 2001/0011164 A1 | 8/2001 | Bierman |
| 2002/0068904 A1 | 6/2002 | Bierman et al. |
| 2002/0099360 A1 | 7/2002 | Bierman |
| 2002/0133121 A1 | 9/2002 | Bierman |
| 2002/0177816 A1* | 11/2002 | Brimhall .......... A61M 25/0637 604/174 |
| 2003/0055382 A1 | 3/2003 | Schaeffer |
| 2003/0229313 A1 | 12/2003 | Bierman |
| 2004/0102736 A1 | 5/2004 | Bierman |
| 2004/0111067 A1 | 6/2004 | Kirchhofer |
| 2004/0138624 A1 | 7/2004 | Bierman |
| 2004/0204685 A1 | 10/2004 | Wright et al. |
| 2005/0182367 A1 | 8/2005 | Walborn |
| 2005/0215953 A1 | 9/2005 | Rossen |
| 2005/0251157 A1 | 11/2005 | Saadat et al. |
| 2005/0288635 A1 | 12/2005 | Davis et al. |
| 2006/0015076 A1 | 1/2006 | Heinzerling et al. |
| 2006/0064063 A1 | 3/2006 | Bierman |
| 2006/0135944 A1 | 6/2006 | Bierman |
| 2006/0184127 A1 | 8/2006 | Bierman |
| 2006/0184129 A1 | 8/2006 | Bierman |
| 2006/0217669 A1 | 9/2006 | Botha |
| 2006/0247577 A1 | 11/2006 | Wright |
| 2006/0264836 A1 | 11/2006 | Bierman |
| 2006/0270994 A1* | 11/2006 | Bierman .............. A61M 25/02 604/180 |
| 2006/0270995 A1 | 11/2006 | Bierman |
| 2007/0173766 A1 | 7/2007 | Bierman |
| 2008/0125718 A1 | 5/2008 | Tsuchiya et al. |
| 2008/0132848 A1 | 6/2008 | Wright et al. |
| 2009/0143740 A1* | 6/2009 | Bierman ............. A61M 5/1415 604/177 |
| 2010/0179482 A1 | 7/2010 | Wright et al. |
| 2010/0324491 A1 | 12/2010 | Bierman et al. |
| 2012/0136314 A1* | 5/2012 | Ciccone ............... A61M 25/02 604/174 |
| 2012/0232488 A1 | 9/2012 | Aviles |
| 2020/0215309 A1 | 7/2020 | Ciccone |

FOREIGN PATENT DOCUMENTS

| | | |
|---|---|---|
| EP | 0064284 A2 | 11/1982 |
| EP | 0356683 A1 | 3/1990 |
| EP | 2470251 B1 | 12/2014 |
| FR | 2381529 A1 | 9/1978 |
| FR | 2922458 A1 | 4/2009 |
| GB | 2086466 A | 5/1982 |
| GB | 2211417 A | 7/1989 |
| WO | 8001458 A1 | 7/1980 |
| WO | 9412231 A1 | 6/1994 |
| WO | 9421319 A1 | 9/1994 |
| WO | 9715337 A1 | 5/1997 |
| WO | 9955409 A1 | 11/1999 |
| WO | 00/48658 A1 | 8/2000 |
| WO | 2004016309 A2 | 2/2004 |
| WO | 2004022140 A1 | 3/2004 |
| WO | 2007024900 A2 | 3/2007 |
| WO | 2007117655 A2 | 10/2007 |
| WO | 2008151047 A1 | 12/2008 |
| WO | 2011025478 A1 | 3/2011 |
| WO | 2011133818 A1 | 10/2011 |

OTHER PUBLICATIONS

CA 2,737,640 filed Sep. 18, 2012 Office Action dated Jul. 25, 2016.
PCT/US03/25622 filed Aug. 15, 2003 International Search Report dated Mar. 10, 2004.
PCT/US2009/054955 filed Aug. 25, 2009 International Search Report and Written Opinion dated May 17, 2010.
PCT/US2009/057566 filed Sep. 18, 2009 International Search Report and Written Opinion dated Nov. 16, 2009.

(56) References Cited

OTHER PUBLICATIONS

PCT/US2010/044016 filed Jul. 30, 2010 International Preliminary Report on Patentability dated Feb. 5, 2013.
PCT/US2010/044016 filed Jul. 30, 2010 International Search Report and Written Opinion dated Sep. 24, 2010.
U.S. Appl. No. 11/837,472, filed Aug. 10, 2007, Final Office Action dated May 10, 2016.
U.S. Appl. No. 11/837,472, filed Aug. 10, 2007, Non-Final Office Action dated Oct. 2, 2015.
U.S. Appl. No. 11/837,472, filed Aug. 10, 2007, Final Office Action dated Jun. 11, 2015.
U.S. Appl. No. 13/813,102, filed Sep. 10, 2013 Advisory Action dated Nov. 22, 2016.
U.S. Appl. No. 13/813,102, filed Sep. 10, 2013 Board Decision dated Sep. 25, 2019.
U.S. Appl. No. 13/813,102, filed Sep. 10, 2013 Examiner's Answer dated May 8, 2017.
U.S. Appl. No. 13/813,102, filed Sep. 10, 2013 Final Office Action dated Jun. 29, 2020.
U.S. Appl. No. 13/813,102, filed Sep. 10, 2013 Final Office Action dated Sep. 27, 2016.
U.S. Appl. No. 13/813,102, filed Sep. 10, 2013 Non-Final Office Action dated Apr. 22, 2016.
U.S. Appl. No. 13/813,102, filed Sep. 10, 2013 Notice of Allowance dated Feb. 3, 2021.
U.S. Appl. No. 14/285,460, filed May 22, 2014 Advisory Action dated Aug. 14, 2017.
U.S. Appl. No. 14/285,460, filed May 22, 2014 Examiner's Answer dated Nov. 1, 2018.
U.S. Appl. No. 14/285,460, filed May 22, 2014 Final Office Action dated May 24, 2017.
U.S. Appl. No. 14/285,460, filed May 22, 2014 Non-Final Action dated Feb. 7, 2018.
U.S. Appl. No. 14/285,460, filed May 22, 2014 Non-Final Office Action dated May 30, 2019.
U.S. Appl. No. 14/285,460, filed May 22, 2014 Non-Final Office Action dated Nov. 25, 2016.
U.S. Appl. No. 14/285,460, filed May 22, 2014 Notice of Allowance dated Sep. 25, 2019.
U.S. Appl. No. 16/818,902, filed Mar. 13, 2020 Non-Final Office Action dated Sep. 16, 2022.
U.S. Appl. No. 16/818,902, filed Mar. 13, 2020 Notice of Allowance dated Jan. 30, 2023.

* cited by examiner

SECUREMENT DEVICE

PRIORITY

This application is a continuation of U.S. patent application Ser. No. 13/813,102, filed Sep. 10, 2013, now U.S. Pat. No. 11,020,565, which is a U.S. national stage application from International Application No. PCT/US2010/044016, filed Jul. 30, 2010, each of which is incorporated by reference in its entirety into this application.

BACKGROUND OF THE INVENTION

Field of the Invention

This invention relates to a securement system used to attach a medical article to a patient.

Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical article properly positioned for the duration of treatment, the catheter or medical article can be secured to the patient in a variety of ways. Most commonly, this involves taping or suturing the catheter or medical article to the patient.

Securing a catheter with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheter upon the patient.

Taped dressings also require periodic changes. The frequent, often daily, removal and reapplication of adhesive tape to the skin of the patient can excoriate the skin. Such repeated applications of tape over the catheter or medical article can additionally lead to the buildup of adhesive residue on the outer surface of the catheter or medical article. This residue can result in contaminants adhering to the medical article itself, increasing the likelihood of infection of the insertion site. This residue can also make the catheter or medical article stickier and more difficult to handle for healthcare providers.

Suturing also carries risk, both to healthcare workers and patients. Healthcare workers can suffer accidental needlestick injury, which may expose them to hepatitis, HIV, and other pathogens. Patients can suffer local or even systemic infection from suture, as well as scarring and pain.

Portions of certain medical articles, such as catheters, may comprise soft, flexible material, complicating securement of these articles. The flexibility of components of these medical articles can lead to flexure or motion of a secured medical article relative to the insertion site. An improved system that provides secure mechanical fixation of such medical articles without unnecessary manipulation of the medical article after insertion and without undesirable flexure or motion relative to an insertion site is desired for securement of such catheters and other medical articles.

SUMMARY OF THE INVENTION

In one embodiment, a securement device for securing a medical article is provided, the securement device including first and second anchor pads, each including an upper foam layer and a lower adhesive surface, the lower adhesive surface being configured to attach to an epidermal layer of a patient, and a retainer including, a body member having an inverted channel formed therethrough, the inverted channel being configured to retain a portion of the medical article and having a longitudinal access opening disposed on an underside of the body member to allow ingress and egress of the portion of the medical article, first and second anchor pads underlying the body member and laterally offset in opposite directions from the longitudinal access opening, first and second proximal members extending generally transversely downward from the body member and defining a proximal retention surface therebetween, where the first proximal member terminates in a first proximal footing which is secured to the first anchor pad and the second proximal member terminates in a second proximal footing secured to the second anchor pad, first and second distal members extending generally transversely downward from the body member and defining a distal retention surface therebetween, where the first proximal member terminates in a first distal footing which is secured to the first anchor pad, and where the second proximal member terminates in a free end unsecured to an anchor pad, and an offset member extending laterally outward and longitudinally proximal from a point on the body member, the offset member having a downwardly extending portion at its outer end, the downwardly extending portion terminating in a second distal footing which is secured to the first anchor pad.

In another embodiment, a system for securing a medical article is provided, the system including a retainer, the retainer including a proximal pair of upwardly extending members defining a proximal retention surface therebetween, first and second raised proximal portions extending along a proximal edge of the retainer, a distal pair of upwardly extending members defining a distal retention surface therebetween, first and second raised distal portions extending along a distal edge, and a medical article, the medical article including a longitudinally extending central body, a pair of laterally extending wings extending outward from the central body, and an outwardly extending member extending laterally outward and longitudinally distal from the central body, at least a portion of the central body being retained by the proximal and distal retention surfaces of the retainer.

In another embodiment, a retainer for securing a medical article, the retainer including a base having an upper surface tilted at a downward angle in a proximal direction, the base comprising a longitudinally extending depression formed therein. The retainer further includes a retention structure. The retention structure includes a substantially cylindrical channel extending between proximal and distal ends, a first portion of the channel being movable in a generally transverse direction relative to a second portion of the channel.

In another embodiment, a securement device is provided for receiving a medical article having an elongated body, a pair of wings, and a side lumen, the side lumen extending through at least a portion of one of the pair of wings, the securement device including a body member having a first pair of footings, a second pair of footings, and an arm member, each of the first and second pairs of footings defining a retention surface for receiving a portion of the elongated body of the medical article therebetween, at least one of the first pair of footings and at least one of the second pair of footings defining a side opening in the body member, the side opening receiving at least a portion of one of the pair of wings and at least a portion of the side lumen when the medical article is secured within the body member, the arm member defining a side channel at least partially aligned with the side opening, the side channel receiving at least a portion of the side lumen when the medical article is secured within the body member, and at least one anchor pad supporting the body member.

DETAILED DESCRIPTION OF THE PREFERRED EMBODIMENTS

The following description and the accompanying figures, which describe and show the preferred embodiments, are made to demonstrate several possible configurations that a securement system can take to include various aspects and features the invention. Those of skill in the art will recognize that the disclosed aspects and features of the invention are not limited to any particular embodiment of a securement system, and securement systems, which include one or more of the inventive aspects and features herein described, can be designed for use with a variety of medical articles.

Figure 1:
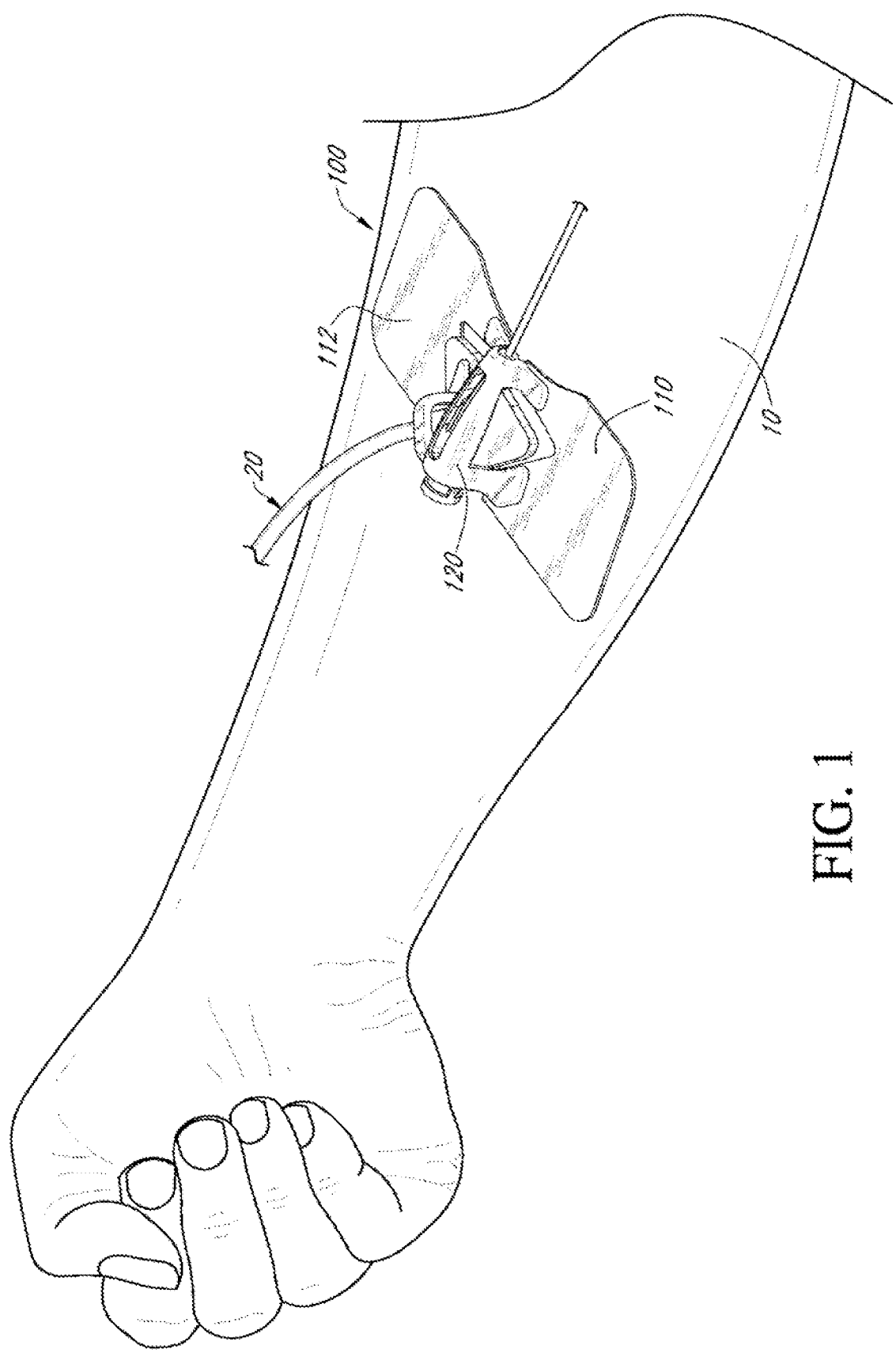
FIG. 1 is a perspective view of a securement device having a medical article retained therein in accordance with a preferred embodiment of the present invention.

To assist in the description of these components of the securement system, the following coordinate terms are used (see FIG. 1). A "longitudinal axis" is generally parallel to a portion of the medical article retained by the securement system, as well as parallel to the axis of a channel of the retainer, through which the medical article extends. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or connector fitting, and therefore is substantially synonymous with the term "longitudinal" as used herein.

Also, the terms "proximal" and "distal", which are used to describe the present securement system, are used consistently with the description of the exemplary applications (i.e., the illustrative examples of the use applications). Thus, proximal and distal are used in reference to the center of the patient's body. The terms "upper," "lower," "top," "bottom," "underside," "upperside" and the like, which also are used to describe the present securement system, are used in reference to the illustrated orientation of the embodiment. For example, the term "upperside" is used to describe the portion of the retainer that is located above a lateral axis that passes through the axis of the channel. The term "underside" is used to describe the portion of the retainer that is located below a lateral axis that passes through the axis of the channel. Brief introductions to some of the features, which are common to the described embodiments of the securement systems, are now described. In the illustrated embodiment, the arrows on the securement device point in the direction toward the insertion site (i.e., in the proximal direction).

The preferred embodiments of the present invention advantageously provide a medical line securement system for securing a medical article to a patient. The medical article preferably has an elongated body and laterally extending wings. The elongated body and laterally extending wings cooperate with a retainer to arrest movement of the medical article in longitudinal, lateral, and transverse directions when placed within the retainer.

In certain embodiments described below, the retainer has a body member which includes an inverted channel formed therethrough. The inverted channel has a longitudinal access opening located on an underside of the retainer to allow ingress or egress of the medical article. The medical article is installed or removed from the underside of the retainer via this access opening. The access opening may be asymmetrical about the longitudinal axis of the securement device to facilitate entry of an asymmetrical medical article. Such an arrangement allows the medical provider to align at least a portion of the medical article with the retainer prior to fixing the retainer to the patient's skin. In this way, the inverted channel retains a portion of the medical article. In other embodiments described below, the retainer has a body member including a non-inverted channel formed therethrough. In such embodiments, the medical article may be installed or removed from the upper side of the medical article, such that the retainer is disposed between the medical article and the patient's skin. In this embodiment, the medical article may be installed or removed after fixing the retainer to the patient's skin. In further embodiments, the medical article may be inserted generally along the longitudinal axis of the securement device.

The retainer of each embodiment described below further includes at least one support that is preferably disposed on the underside of the retainer at a position lower than the access opening. With this construction, the retainer holds the retained portion of medical article away from the patient's skin, when the retained portion is positioned within the retainer channel, to avoid chaffing or excoriating the skin. The support in certain of the illustrated embodiments includes mounting feet that are integral with the body member and are attached to left and right anchor pads. The lower surfaces of the left and right anchor pads attach to the patient's skin.

To facilitate a complete understanding of the embodiments, the remainder of the detailed description describes the securement system with reference to the figures, wherein like elements among the embodiments are referenced with like numerals throughout the following description.

FIG. 1 is a perspective view of a securement device 100 configured in accordance with an embodiment of the present invention, and secured to the skin 10 of a patient. In the illustrated embodiment, the securement device comprises a retainer portion 120 attached to a left anchor pad 110 and a right anchor pad 112. The left and right anchor pads 110, 112 are adhered to the skin 10 of the patient.

Figure 2:
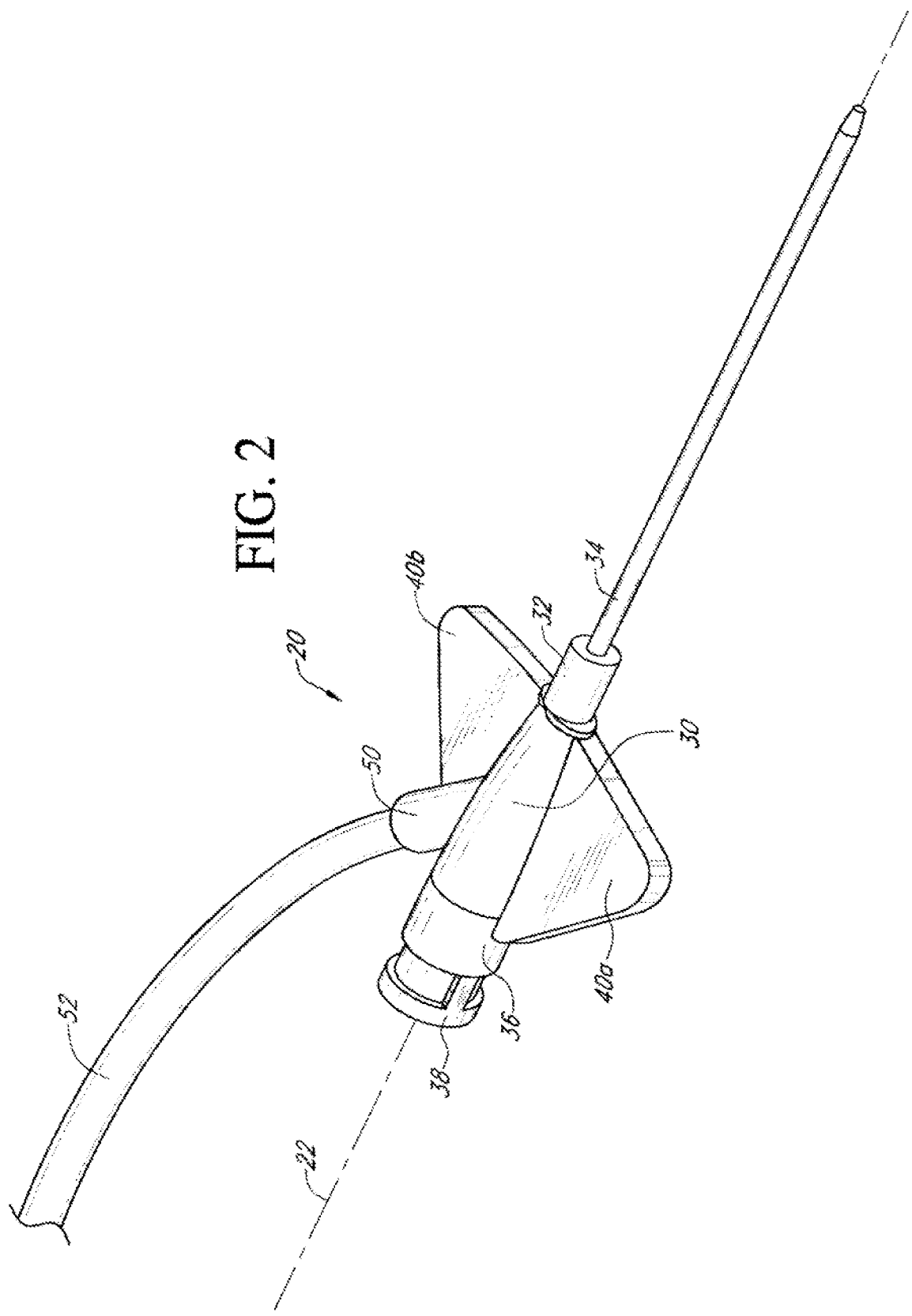
FIG. 2 is a perspective view of the medical article removed from the securement device of FIG. 1.

The securement device 100 in FIG. 1 is shown having a medical article 20 retained therein. FIG. 2 is a perspective view of the medical article 20 retained in the securement device of FIG. 1. The medical article 20 comprises a catheter having wings 40a and 40b extending laterally outward from the central axis 22 of the catheter. In certain embodiments, these laterally extending wings may comprise a flexible material or a combination of a flexible material with a less flexible spine. The spine may be disposed on the surface of the wings or embedded within the wings.

The medical article 20 further includes a longitudinally extending central body 30, a longitudinally extending tip 34 at the proximal end of the medical article, and a distal end 38 which may include connection features for additional devices or structures, such as a needle grip and push tab assembly (not shown). Suitable materials for the body 30 include, but are not limited to, thermoplastic resins such as fluorinated ethylene propylene (FEP), polytetrafluoroethylene (PTFE), polyurethane and the like. The body 30 may comprise a material that is less flexible than the wings 40a, 40b.

The medical article includes a first substantially cylindrical section 32 located at or near the proximal end of the central body 30, and a second substantially cylindrical section 36 located at or near the distal end of the central body 30. Although described as substantially cylindrical, the diameter of these first and second sections 32 and 36 may vary somewhat over the length of the substantially cylindrical sections. A linear variation in the diameter of these sections will result in the section having a frustroconical shape, and a non-linear variation in the diameter of these sections will result in the section having a curved profile.

The medical article 20 further includes section 50 which extends laterally outward and longitudinally back in a distal direction from a portion of the central body 30. In the illustrated embodiment, the outwardly extending portion 50 forms roughly a 45 degree angle with the central body 30, although other embodiments of medical articles 20 may include an outwardly extending portion that is oriented at a different angle, including extension transversely upward or downward from the central body 30. This outwardly extending portion may provide a luminal path between the tip of the catheter and tubing 52 connected to the proximal end of the outwardly extending portion 50. Because the outwardly extending portion is oriented at an angle to the central axis 22 of the medical article 20, the bend in the luminal path allows insertion of a needle along the central axis 22 of the medical article 20, such as from the distal end 38 of the medical article 20.

Examples of such medical articles in which portions of the medical article comprise a flexible material include the commercially available BD NEXIVA™ flexible winged catheters, which include flexible wing structures. Because a large portion of the medical article 20 comprises a flexible material, mechanical fixation between a securement device and the flexible portions of the medical article 20 may be difficult due to the possible deformation of the flexible portions of the medical article 20 and resulting movement of the catheter tip 34.

Figure 3:
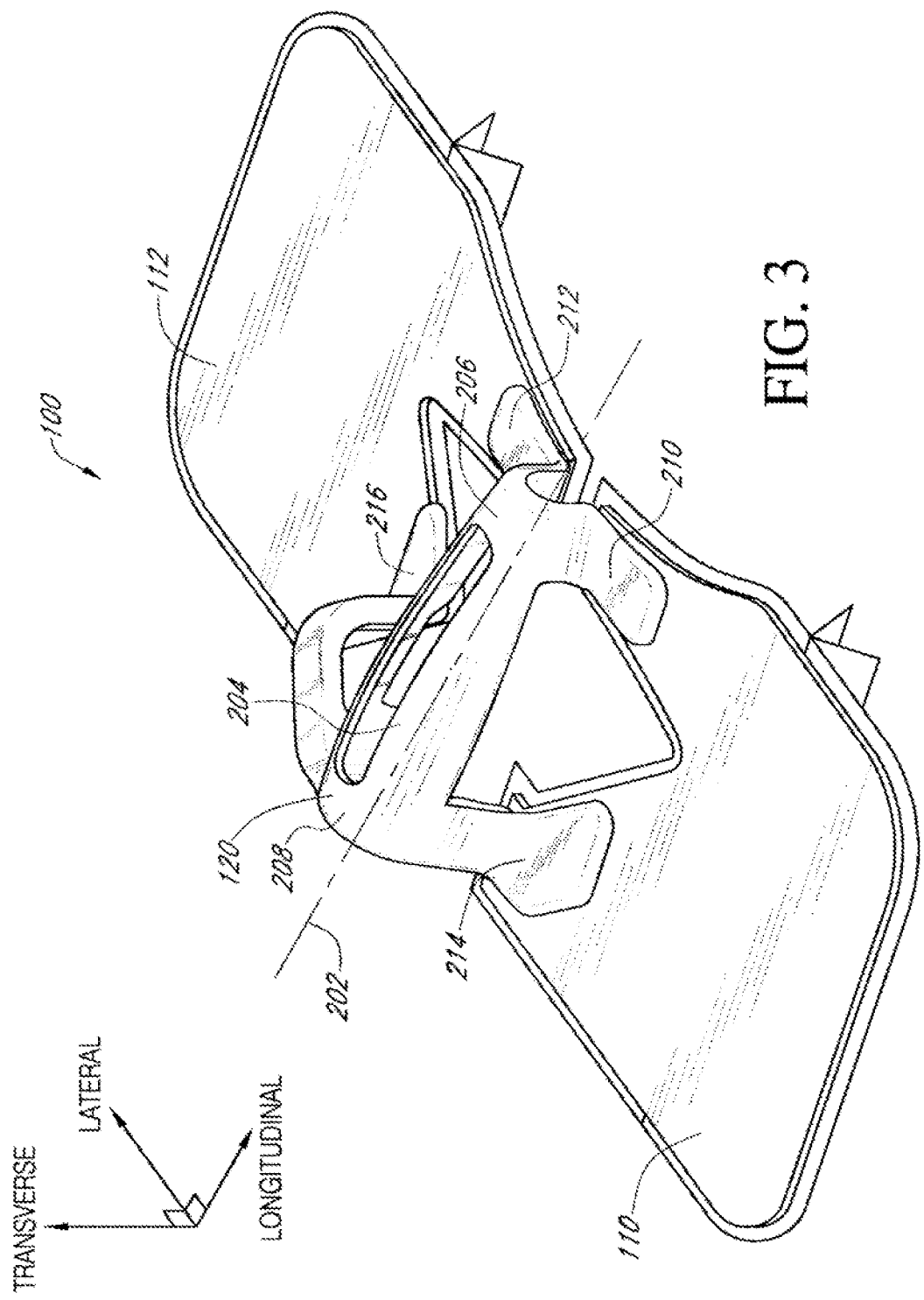
FIG. 3 is a perspective view of the securement device of FIG. without the medical article.
Figure 4:
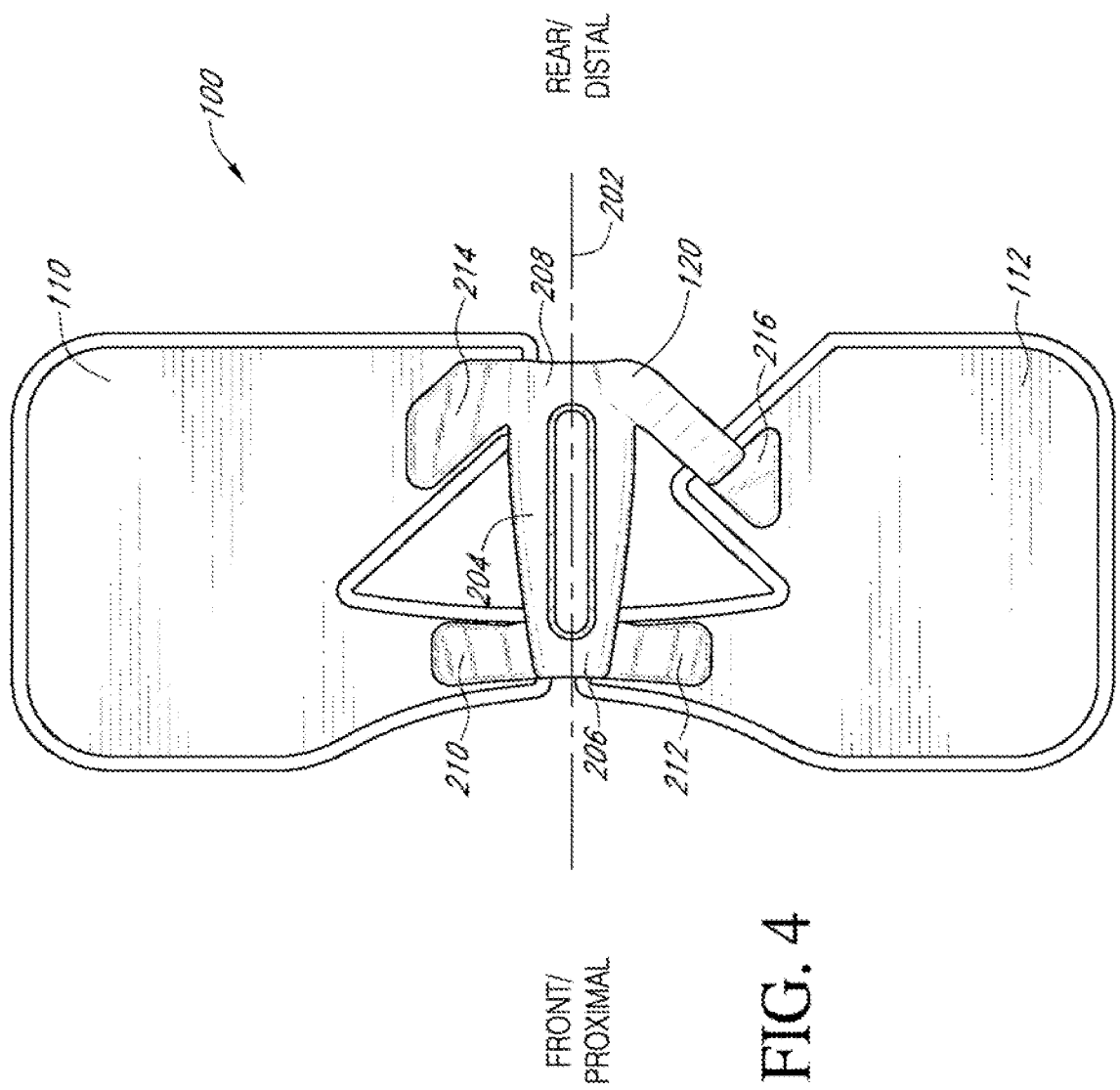
FIG. 4 is a top plan view of the securement device of FIG. 3.

FIG. 3 is a perspective view of the securement device 100 of FIG. 1, and FIG. 4 is a top plan view of the same. As shown in FIGS. 1, 3, and 4, the illustrated securement device 100 comprises three main components: two anchor pads 110, 112, and a retainer 120. The illustrated retainer 120 includes four footings: a front left footing 210, a front right footing 212, a back left footing 214, and a back right footing 216. Each of the left footings 210 and 214 is disposed upon the left anchor pad 110, and each of the right footings 212 and 216 is disposed upon the right anchor pad 112. Each of the footings 210, 212, 214, and 216 is laterally offset from a central or longitudinal axis 202 of the retainer 120. The retainer 120 further includes a central body 204 supported by the footings 210, 212, 216, and 218 and extending generally about the central axis 202 of the retainer. The central body 204 includes a front or proximal portion 206 and a back or distal portion 208.

Figure 5:
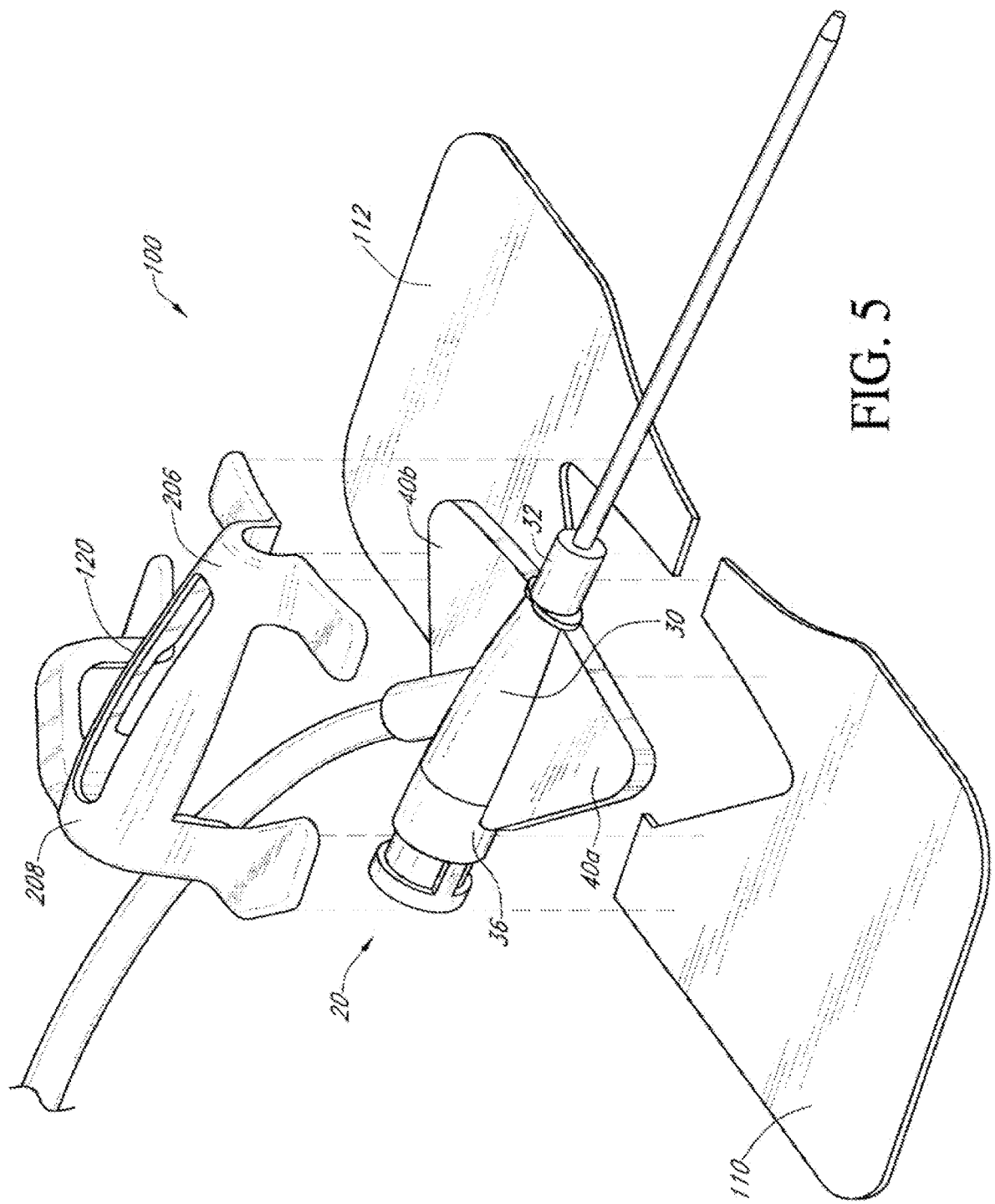
FIG. 5 is an exploded assembly view of the medical article of FIG. 2 aligned with the securement device of FIG. 3.

FIG. 5 is an exploded assembly view of the securement device 100 of FIGS. 1, 3, and 4 in which the retainer 120 is aligned with the medical article 20 to be retained therein. For the purposes of illustration, the retainer 120 is shown as detached from the anchor pads 110 and 112, although in practice, the securement device will typically be provided with the retainer 120 secured to the anchor pads 110 and 112. As noted above, the securement device 100 can form a component of a catheterization or securement system that also includes one or more medical articles, such as connector fittings, catheters, hubs, catheter adaptors, fluid supply lines, or other articles suitable for securement via the anchor pads and retainer. It can be seen that the interior edges of the anchor pads facing one another define an opening which permits the wings 40a and 40b of the medical article to pass upwardly therethrough. The securement device 100 thus permits a medical article such as medical article 20 to be brought upward from beneath the medical article through the space between the anchor pads 110 and 112 to contact the retainer 120. The retainer 120 is generally dimensioned such that the first substantially cylindrical section 32 of the medical article 20 can be brought into contact with the front portion 206 of the retainer 120 while the second substantially cylindrical section 36 of the medical article 20 can be brought into contact with the back portion 208 of the retainer 120.

After the medical article 20 is secured within the retainer 120, the anchor pads 110, 112 are then secured to the skin of the patient, generally by an adhesive disposed upon the bottom surface of the pads. In this way, the retainer 120 secures the medical article to the patient. Thus, the retainer 120 at least restricts, if not prevents, lateral and transverse movement of the retained section of the medical article. Additional features of the securement device 100 can restrict, if not prevent, longitudinal and rotational movement of the retained section of the medical article. The embodiment illustrated is preferably for use with a medical article as described with reference to FIG. 2. The embodiments of the anchor pad and the retainer are described in more detail below.

Figure 6:
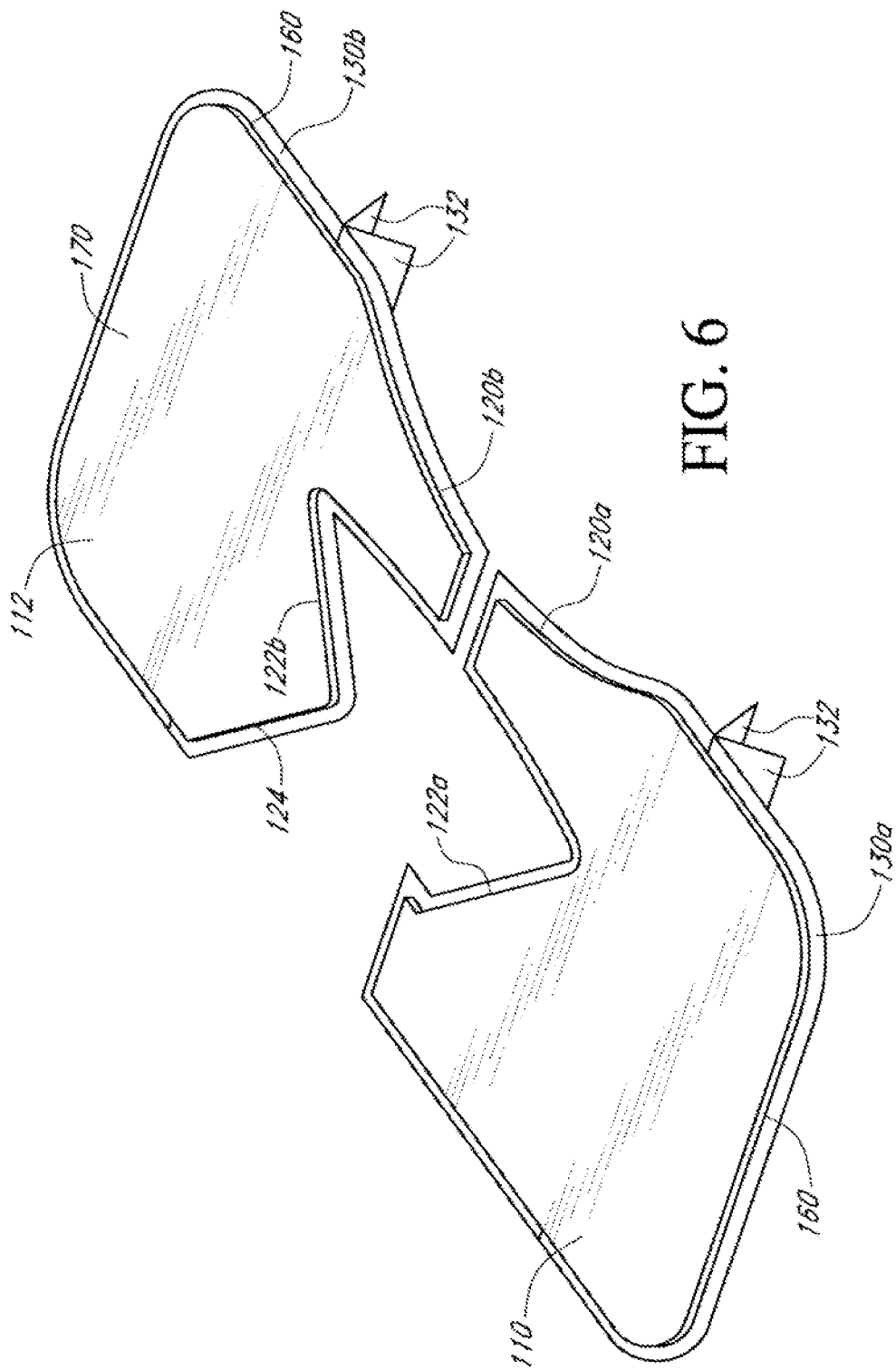
FIG. 6 is a perspective view of the anchor pad from the securement device of FIG. 3.

FIG. 6 illustrates the anchor pads 110 and 112, respectively, apart from the rest of the securement device 100. Each of anchor pads 110 and 112 comprise a generally scalloped region 120a, 120b located at the interior forward corner of each anchor pad. The scalloped configuration eases the process of aligning the securement device 100 with a catheter insertion site in the patient's skin. Anchor pads 110 and 112 also comprise a substantially triangular cutout 122a or 122b on their interior edges to permit passage of portions of medical devices such as flexible wings 40a and 40b. Right anchor pad 112 further comprises an angled edge 124 at the distal interior corner of anchor pad 112 to permit the passage of outwardly extending portion 50 of medical device 20 and the connected tubing 52. Thus, the anchor pads 110 and 112 are sized and dimensioned so that a medical article 20 can pass between them in a generally transversely upward direction. Although only a single shape of the anchor pad is illustrated in FIG. 6, those of skill in the art will recognize that a variety of shapes can be used. For example, the interior cutouts may comprise different sizes or shapes to accommodate a variety of medical articles.

Each anchor pad 110, 112 desirably comprises a laminate structure with an upper plastic (e.g., Tricot woven polyester), paper or foam layer (e.g., closed-cell polyethylene foam) and a lower adhesive layer. The lower adhesive layer constitutes a lower surface 160 of the anchor pad. The lower surface 160 desirably is a medical-grade adhesive and can be either diaphoretic or nondiaphoretic, depending upon the particular application. Such foam with an adhesive layer is available commercially from Avery Dennison of Painsville, Ohio. While not illustrated, the anchor pads 110, 112 can include suture holes in addition to the adhesive layer to further secure the anchor pad to the patient's skin.

In other variations, a hydrocolloid adhesive or zinc oxide-based adhesive can advantageously be used upon the anchor pads 110, 112 for attaching the anchor pads to the skin of the patient. The hydrocolloid or zinc oxide-based adhesive can be used either alone or in combination with another medical grade adhesive (e.g., in combination with the adhesive available from Avery Dennison). Hydrocolloid and zinc oxide-based adhesives have less of a tendency to excoriate the skin of a patient when removed. This can be particularly important for patients whose skin is more sensitive or fragile, such as neonates and those with a collagen deficiency or other skin related condition.

In another variation, each anchor pad 110, 112 comprises a laminate structure with an upper woven layer and a lower adhesive layer. The upper layer can be polyester or other suitable polymer or textile materials. One particular suitable material is woven polyester available commercially under the name "Tricot" from Tyco. The lower adhesive layer constitutes the lower surface 160 of the anchor pad. The lower surface desirably is a medical-grade adhesive and can be either diaphoretic or nondiaphoretic, depending upon the particular application.

A surface of the upper foam layer constitutes an upper surface 170 of the anchor pads 110, 112. The upper surface 170 can be roughened by corona-treating the foam with a low electric charge. The roughened or porous upper surface can improve the quality of the adhesive joint (which is described below) between the footings 210, 212, 216, and 218 and the anchor pads 110, 112. In a further variation, the flexible anchor pad can comprise an upper paper or other woven or nonwoven cloth or plastic layer in lieu of a roughened upper foam surface.

As illustrated in FIG. 6, removable release liners 130a and 130b desirably cover the adhesive lower surface 160 before use. The release liners 130a and 130b may comprise paper, plastic, or any other suitable material. The liners 130a and 130b preferably resist tearing and desirably are divided into a plurality of pieces to ease attachment of the pad to a patient's skin.

The liners 130a and 130b comprises folded over portions to define pull tabs 132. The pull tabs 132 can be utilized to remove the release liners 130a and 130b from their adhesive lower surface 160 during application. A healthcare provider uses the pull tab 132 by grasping and pulling on it so that the liners 130a and 130b are separated from the lower surfaces 160 of anchor pads 110 and 112. The pull tabs 132 overcomes any requirement that the healthcare provider pick at a corner edge or other segment of the liner in order to separate the liner from the adhesive layer.

The pull tabs 132 can be designed m a variety of configurations. For example, the pull tab 132 can be located along a center line of the anchor pads 110 and 112; or alternatively, the pull tab can be located along any line of the anchor pads 110 and 112 in order to ease the application of the anchor pad onto the patient's skin at a specific site. In certain embodiments, the pull tabs may extend in a generally longitudinal direction as shown, facilitating grasping of the pull tabs from the back side of the retainer, although the pull tabs may in other embodiments be oriented in a lateral direction, or at any appropriate angle.

It can also be seen that the liners 130a and 130b may be dimensioned to substantially match the shape of the anchor pads 110 and 112, particularly the interior sides 122a and 122b of the anchor pads 110 and 112, including the angled edge 124 at the proximal interior corner of anchor pad 112. In this way, the medical device 20 can be inserted into the retainer 120 before removal of the liners 130a and 130b, without interference from the liners 130a and 130b.

Figure 7:
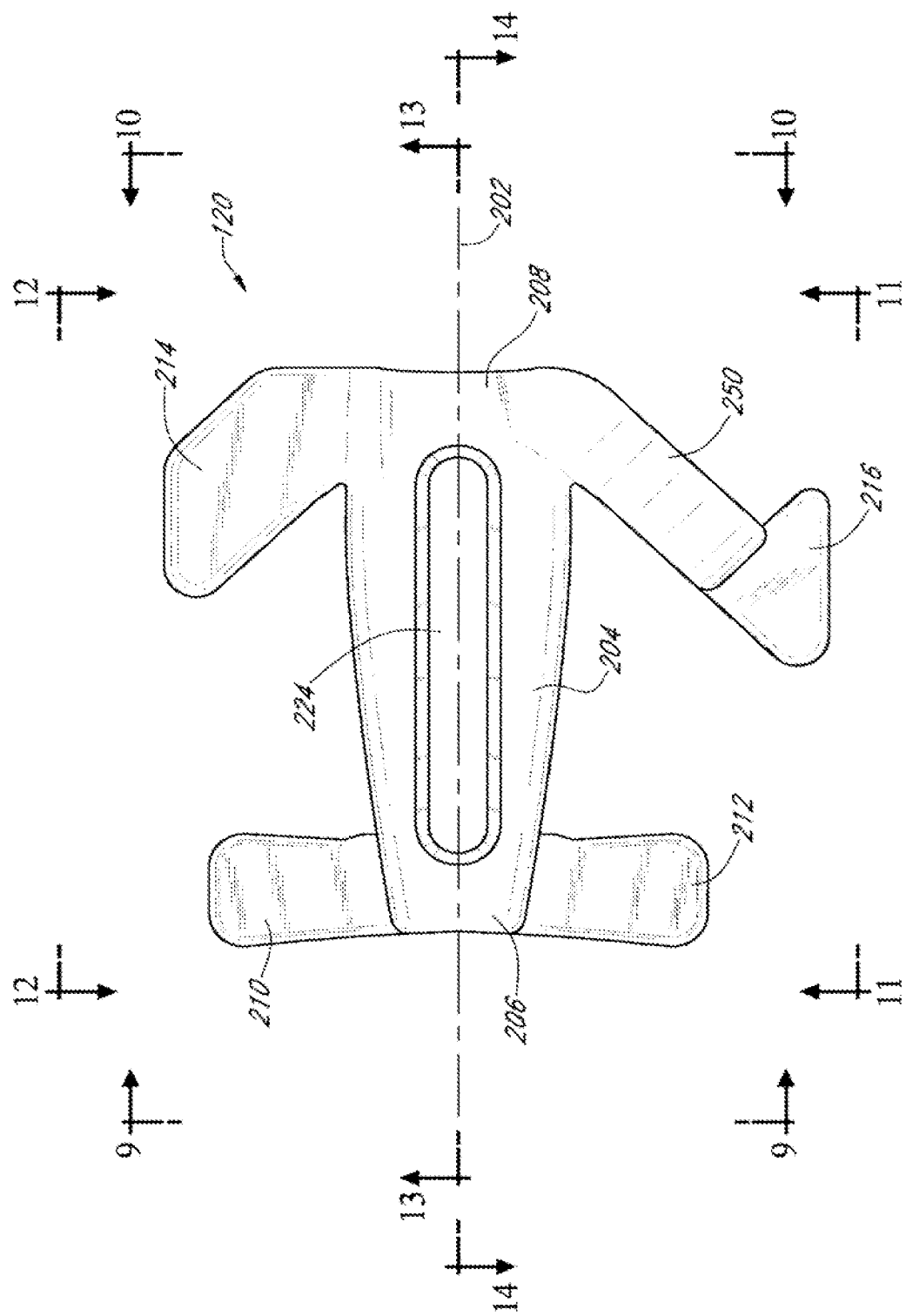
FIG. 7 is a top plan view of the retainer from the securement device of FIG. 3.
Figure 8:
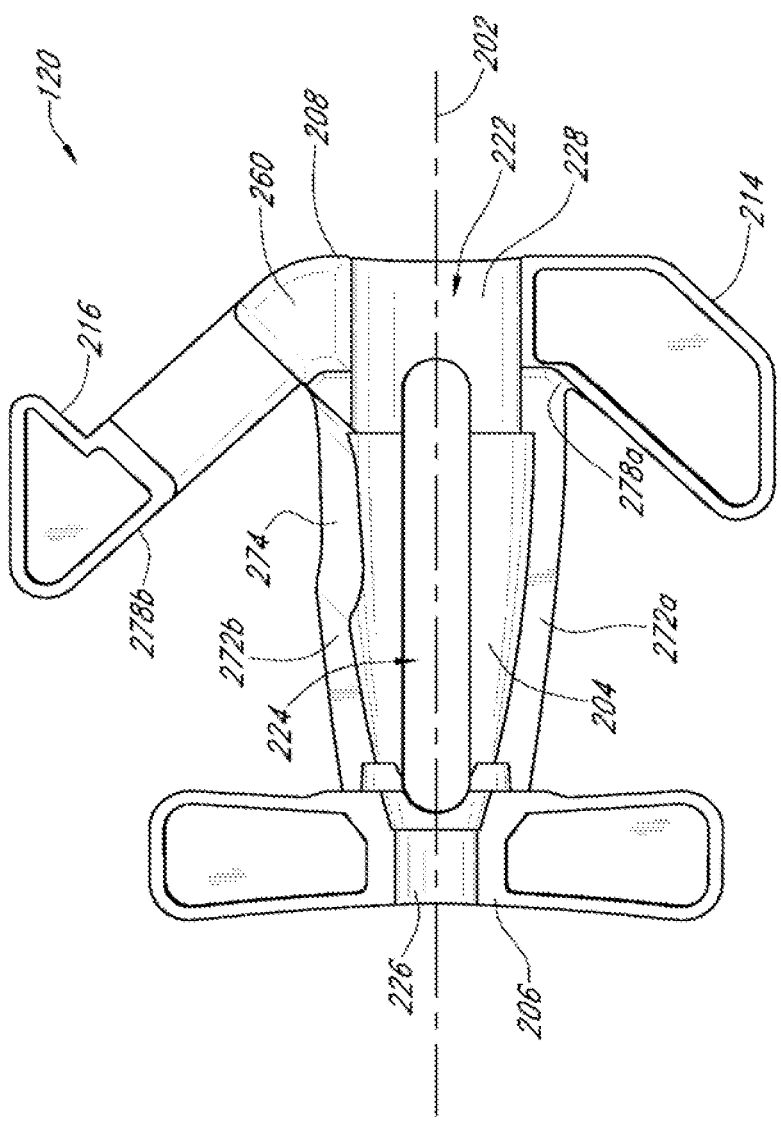
FIG. 8 is a bottom plan view of the retainer of FIG. 7.

An embodiment of the retainer 120 is described with reference to FIGS. 7-14, which illustrate only the retainer 120, detached from the anchor pads. FIG. 7 is a top plan view of the retainer 120 which inhibits at least motion of an installed medical article. In certain embodiments, the retainer 120 arrests movement in the longitudinal, lateral and transverse directions. FIG. 8 is a bottom plan view of the retainer 120.

It can be seen in FIG. 8 that the central body 204 defines an inverted central channel 222 extending along a longitudinal axis 202 of the retainer 120. The front portion 206 of the central body 204 of the retainer 120 comprises a front interior abutment surface 226 located generally laterally between the front left footing 210 and the front right footing 212, and centered along a longitudinal axis 202 of the retainer. Similarly, the back portion 208 of the central body 204 of the retainer 120 comprises a back interior abutment surface 228 laterally offset from the back left footing 214 and centered along the longitudinal axis 202 of the retainer. The central body 204 of the retainer further comprises a longitudinally extending aperture 224 substantially aligned with the longitudinal axis of the retainer, which may facilitate alignment of the retainer 120 with the medical article to be retained during the fixation process, and allow a clear view of the retained catheter or other medical article once the retained medical article is in place on the patient's skin.

Figure 9:
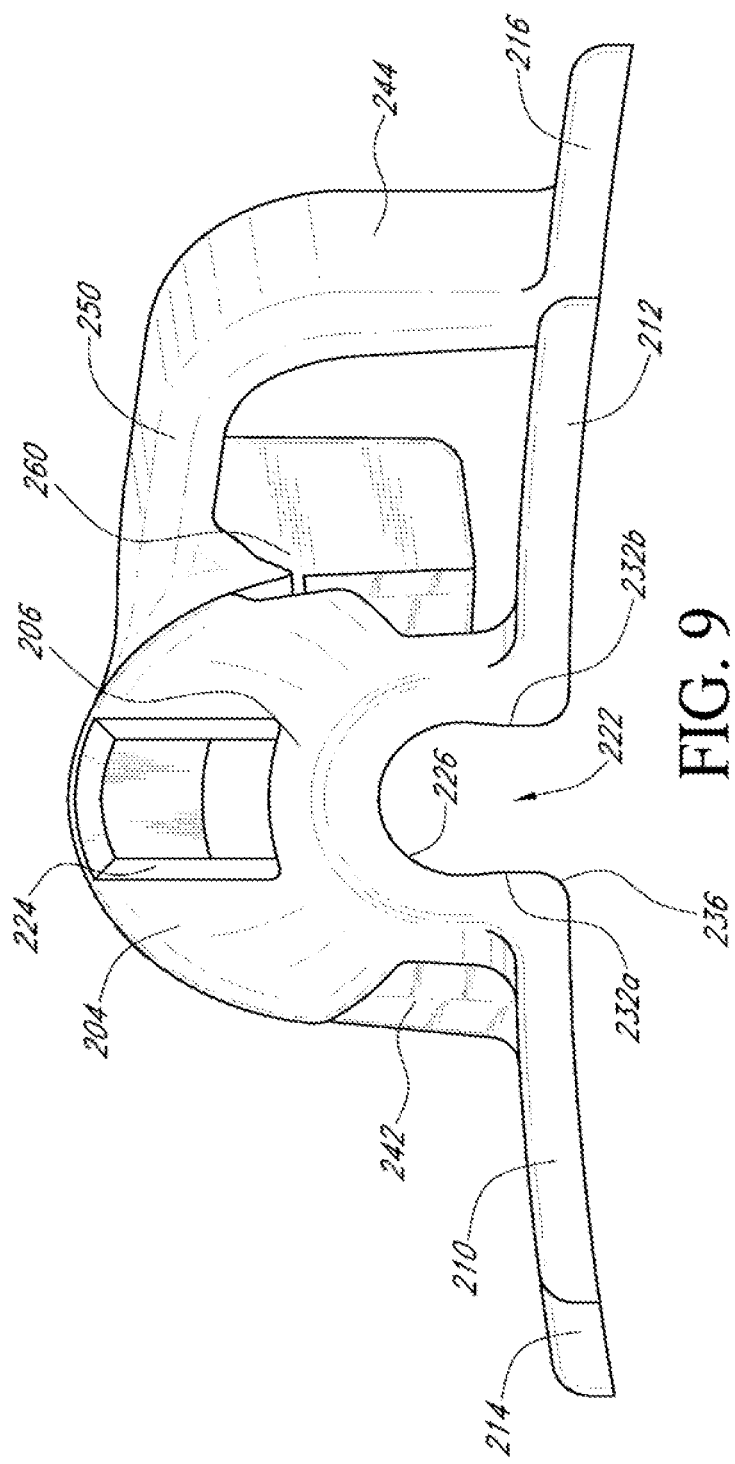
FIG. 9 is a front view of the retainer of FIG. 7.

FIG. 9 is a front view of the retainer 120, illustrating the cross-sectional shape of the central channel 222 at the front of the retainer. The shape of the central channel 222 is defined at the front portion 206 of the retainer 120 by front interior abutment surface 226, which in the illustrated embodiment extends more than 180 degrees about the longitudinal axis 202 of the retainer 120, such that the lowermost portions of front abutment surface 226 are formed by inwardly extending portions 232a and 232b of the retainer, spaced apart from one another at their closest point by a distance which is smaller than the diameter of the overlying section of central channel 222. The difference in width between the diameter of the channel 222 and the distance between the inwardly extending portions 232a and 232b of the retainer allows the retainer to form a snap-fit connection with the retained medical article, such that one or both of the retainer and the medical article can be slightly deformed to allow the metical article to be pressed into the central channel 222, and the inwardly extending portions 232a and 232b can then prevent unintentional transverse movement of the medical article in a downward direction.

Figure 10:
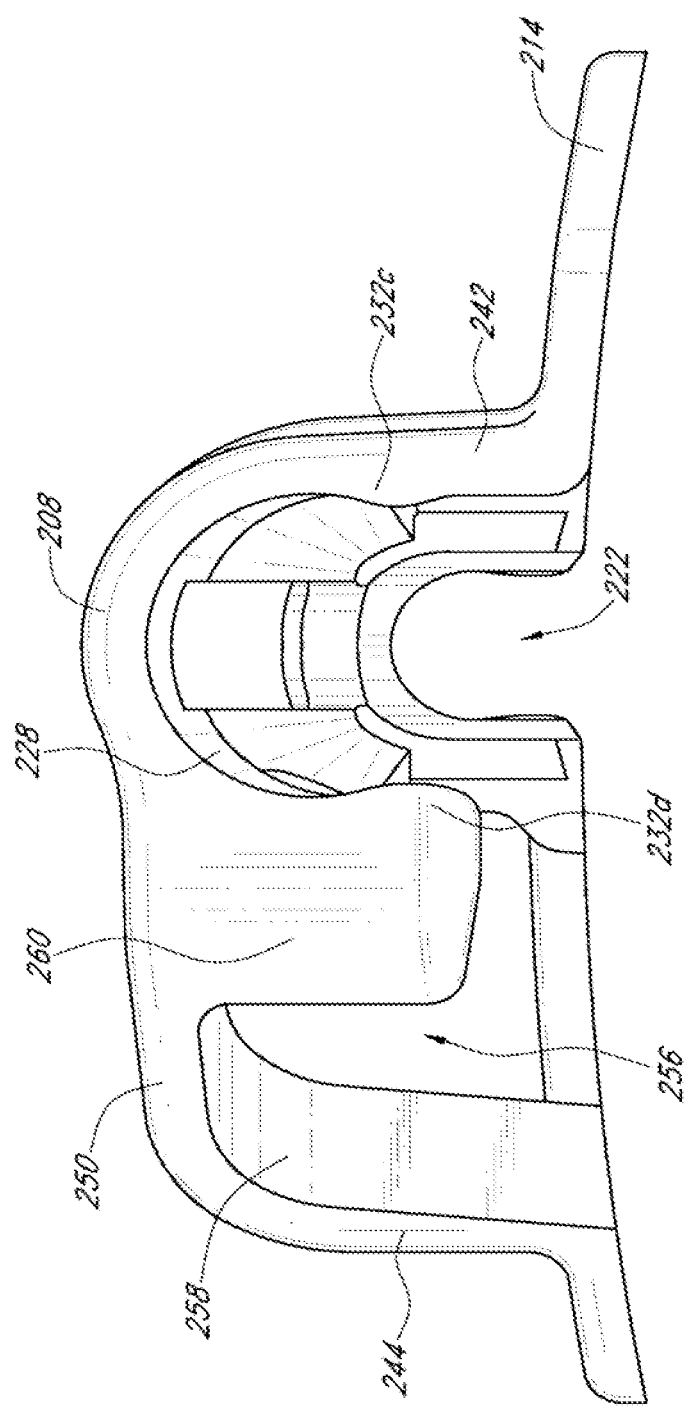
FIG. 10 a back view of the retainer of FIG. 7.

Similarly, FIG. 10 is a back view of the retainer 120, illustrating the cross-sectional shape of the central channel 222 at the back of the retainer. The rear interior abutment surface 228 defines the shape of the central channel at the back portion 208 of the retainer 120. The rear interior abutment surface 228 also extends more than 180 degrees about the longitudinal axis 202 of the retainer 120, and the lowermost portions of rear abutment surface 228 are formed by inwardly extending portions 232c and 232d of the retainer. The rear abutment surface therefore also provides a snap-fit connection with the retained medical article.

It can be seen that of the two inwardly extending surfaces 232c and 232d which form a portion of rear abutment surface 228, left surface 232c extends inwardly from a sidewall 242 extending between the rear portion 208 of central body 204 and left rear footing 214. In contrast, right surface 232d extends inwardly from a downwardly extending portion 260 of the retainer 120 which is not secured at its base to a footing, but is connected only at its top to overlying arm 250 which extends outward from the central body 204 of the retainer. Because the downwardly extending portion 260 is not attached at its base to a footing, the downwardly extending portion 260 may be substantially thicker than the sidewall 242, in order to provide sufficient rigidity and support to rear abutment surface 228 to maintain the snap-fit connection when a medical article is secured therein.

Inner surface contours of portions of the central channel 222 preferably are selected depending on the geometry of the portion of the medical article to be retained. In particular, either of the front abutment surface 226 and rear abutment surface 228 may be configured to provide channel sections with a substantially constant radius along their lengths when the portion of the medical article to be retained has a constant diameter. In other embodiments, when the portion of the medical article to be retained comprises a varying radius, such as a frustroconical shape, the radius of the portion of the central channel 222 defined by one of the abutment surfaces may similarly comprise a varying radius. In the illustrated embodiment, the front and rear abutment surfaces comprise a slight taper, as can best be seen in FIGS. 8 and 10. It can also be seen that the portion of the central channel 222 located between the abutment surfaces 226 and 228 may comprise a widening portion, and in certain embodiments may not serve a retention function. Additional embodiments of the central channel 222 of the retainer can comprise a plurality of different radii and/or tapering regions. By matching the inner surface contour of portions of the central channel 222 to the outer surface of the secured portion of a medical article, a more effective securement may be achieved.

Figure 11:
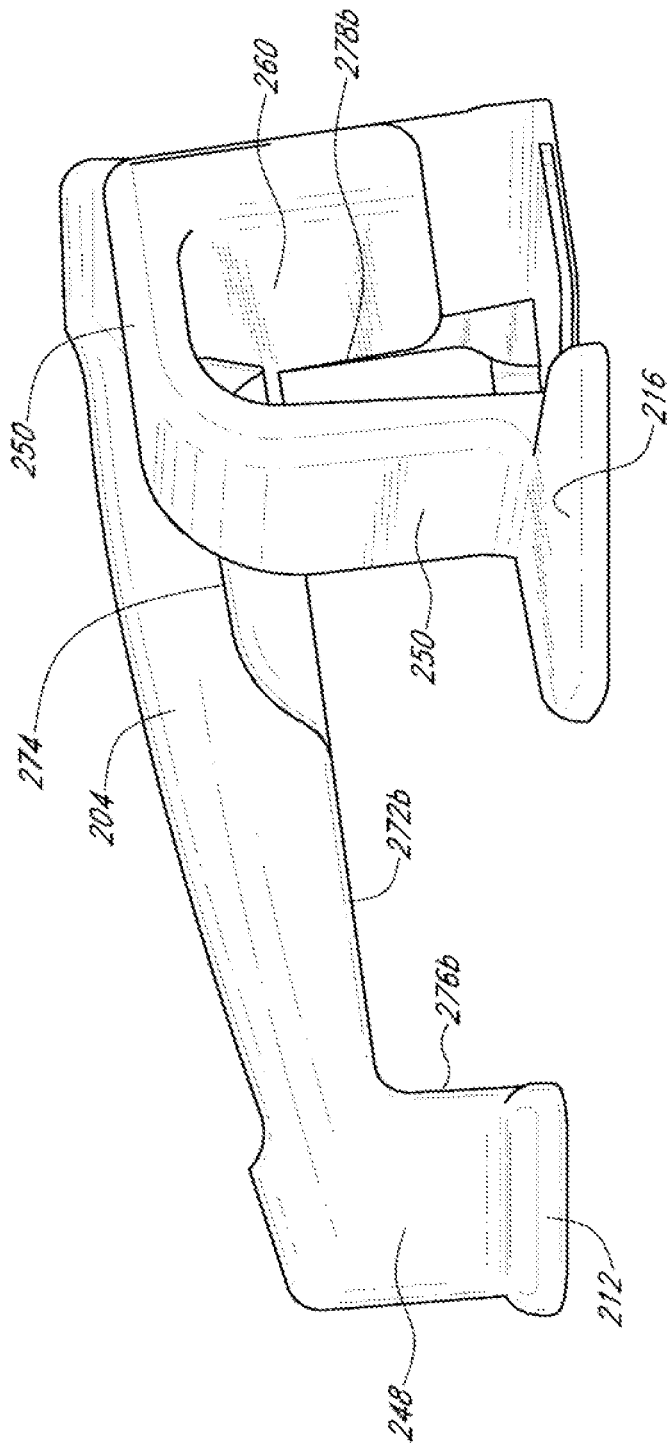
FIG. 11 is a right side view of the retainer of FIG. 7.
Figure 12:
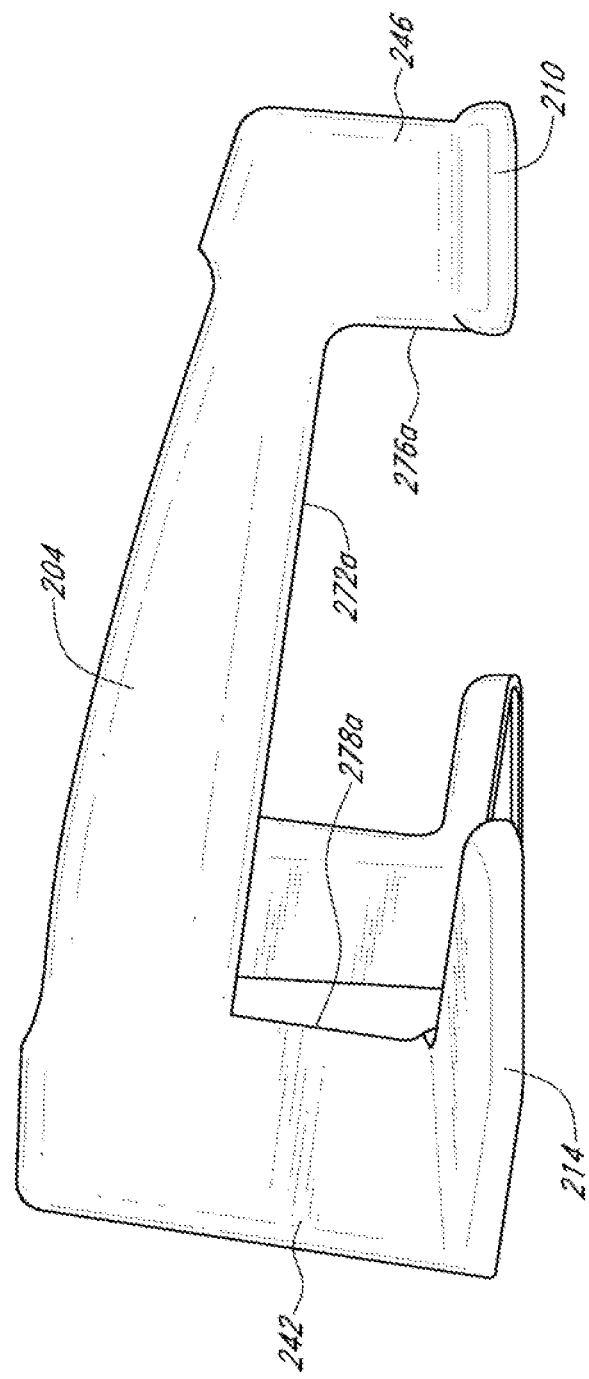
FIG. 12 a left side view of the retainer of FIG. 7.

FIG. 11 is a left side view of the retainer 120, and FIG. 12 is a right side view of the retainer 120. As can best be seen in FIGS. 10 and 12, the outwardly extending arm 250 of the retainer 120 cooperates with sidewall 244 and downwardly extending portion 260 to define a passage 256 which accommodates the outwardly extending portion 50 and tubing 52 of medical article 20 (see FIG. 2). In the illustrated embodiment, the passage 256 is substantially larger than the cross-sectional size of the outwardly extending portion 50 and tubing 52 of the medical article 20, such that the outwardly extending portion 50 and/or tubing 52 can extend through the passage without contacting the interior surface 258 of the passage 256. It can also be seen that the facing surfaces of the sidewall 244 and the downwardly extending portion 260 may be substantially parallel to one another, and may also be substantially parallel to the direction in which the outwardly extending portion 50 of medical device 20 will extend when the medical device is secured within the retainer 50. Such an arrangement may reduce the length of arm 250 of the retainer.

It can also be seen in FIG. 11 that the right side of central body 204 of the retainer 120 comprises a scalloped cutout 274 on the underside of central body 204, to enable the outwardly extending portion 50 of the medical article to pass through. The difference between the height of the scalloped cutout 274 and the height of the lower right edge 272b of the central body 204 may vary based on the particular design of the medical article to be retained.

In the illustrated embodiment, the medical article 20 to be retained comprises a central body 30 having an upper surface which is higher than the upper surface of the outwardly extending portion 50 extending at an angle from the central body 30. The upper surface of the outwardly extending portion 50 is higher than the upper surface of the laterally extending wing 40b through which it extends. Thus, one or both of each of the scalloped cutout 274 and the lower right surface 272b of the central body may serve as abutment surfaces which may restrict rotation of the medical article 20 about its longitudinal axis 22.

In an embodiment in which the height of the scalloped cutout 274 is substantially identical to the height differential between the outwardly extending portion 50 of the medical article and the laterally extending wing 40b, each of the scalloped cutout and surface 272b may contact portions of the medical article and serve as an abutment surface. In an embodiment where the height of the scalloped cutout 274 is greater than the height differential between the outwardly extending portion 50 and the wing 40b, contact between the portion 50 and the scalloped cutout 274 will prevent the wing 40b from contacting the central body of the retainer, and in an embodiment where the height of the scalloped cutout 274 is less than the height differential, contact between the wing 40b and surface 272b will prevent contact between the portion 50 and the scalloped cutout 274.

Similarly, the distal surface 276b of the front right sidewall 248 and the proximal surface 278b of the downwardly extending portion 260 may serve as abutment surfaces which inhibit the longitudinal translation of the medical article 20 relative to the retainer 120. The front right sidewall 248 and the downwardly extending portion 260 allow the wing 40b of the medical article 20 to be positioned therebetween. If the medical article 20 is longitudinally translated within the retainer, the sides of wing 40b may contact one of the surfaces 276b or 278b, preventing further longitudinal translation.

In FIG. 12, it can be seen that the left side of the retainer 120 comprises similar abutment surfaces. Rotation of the device 20 around its longitudinal axis 22 will be inhibited by contact between the upper surface of wing 40a and the lower left surface 272a of the central body 204 of retainer 120. Similarly, the distal surface 276a of left front sidewall 246 and the proximal surface 278a of left rear sidewall 242 constrain lateral translation of the medical article 20 relative to the retainer 120 by contact with the sides of wing 40a.

Figure 13:
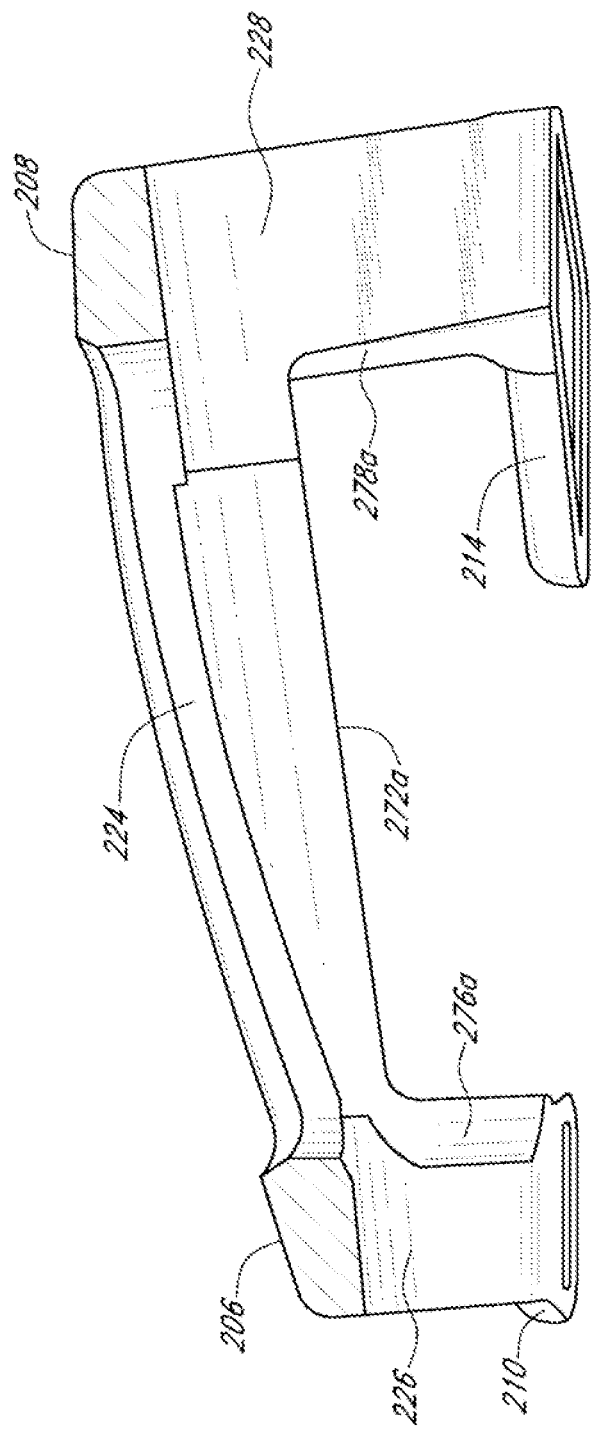
FIG. 13 is a cross-section view of the retainer taken along line 13-13 in FIG. 7.

FIG. 13 is a cross-section view of the retainer 120 taken along line 13-13 in FIG. 7. It can be seen in FIG. 13 that the distal surface 276a of the front left sidewall 246, the lower left surface 272a of the central body 204, and the proximal surface 278a of left rear sidewall 242 cooperate to define an opening through which the laterally extending wing 40a of the medical article 20 may extend. These surfaces may serve as abutment surfaces as described above, depending on the specific dimensions of the medical article 20 relative to the retainer 120.

Figure 14:
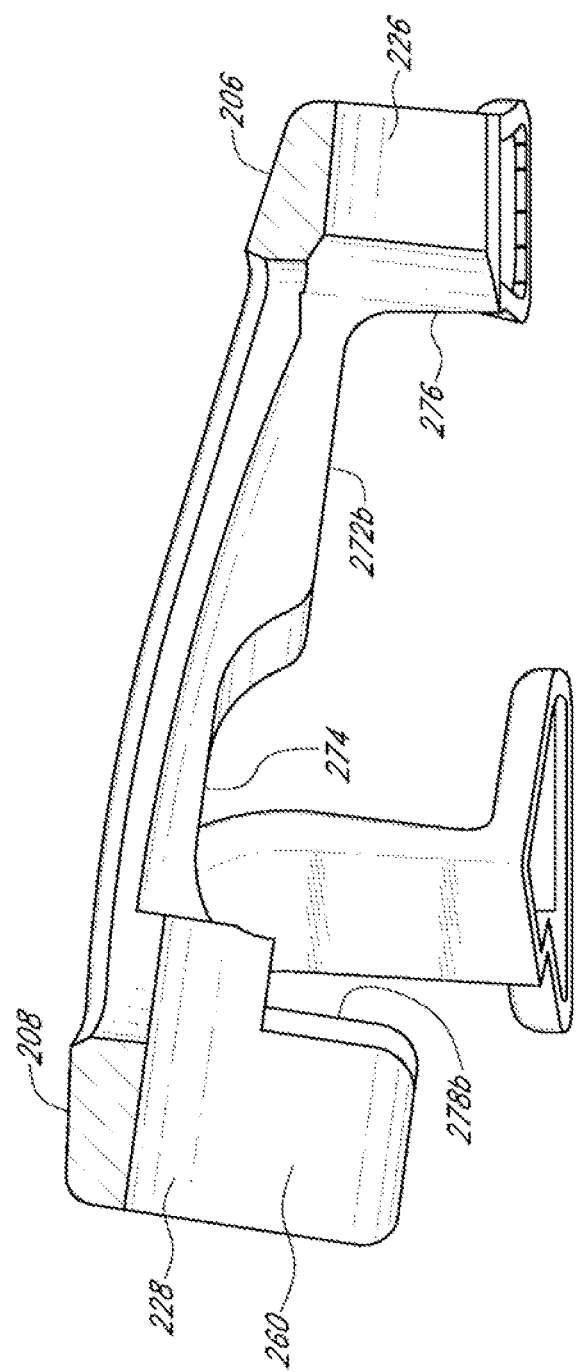
FIG. 14 is a cross-section view of the retainer taken along line 14-14 in FIG. 7.

FIG. 14 is a cross-section view of the retainer 120 taken along line 14-14 in FIG. 7. The distal surface 276b of the front right sidewall 248, the lower left surface 272b of the central body 204, the scalloped cutout 274, and proximal surface 278b of the downwardly extending portion 260 cooperate to define an opening through which the laterally extending wing 40b of the medical article may extend, along with the upper projection of the outwardly extending portion 50 extending above the upper surface of wing 40b. These may also serve as abutment surfaces as described above. In particular, the upper surface of scalloped cutout 274 may further inhibit upward translation of the medical article 20 or rotation about the longitudinal axis of the medical article 20, while the proximal and distal edges may further inhibit longitudinal translation of the article relative to the retainer 120.

Figure 15:
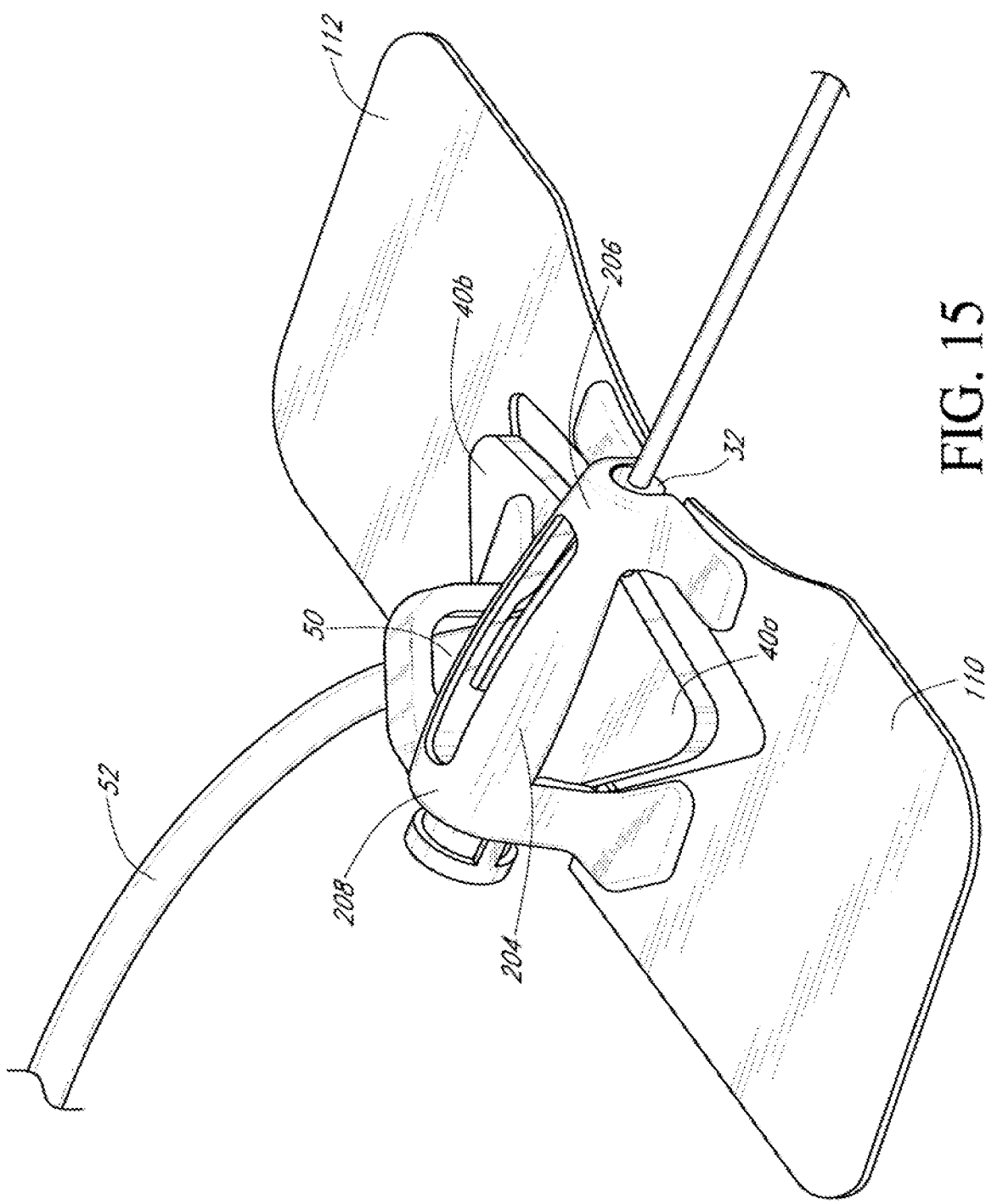
FIG. 15 is a perspective view of the securement device of FIG. 3 with the medical article of FIG. 2 retained therein.

FIG. 15 is a perspective view of the securement device of FIG. 3 with the medical article of FIG. 2 retained therein. The positioning of the retainer within the medical article can be seen in greater detail than in FIG. 1, including the alignment of outwardly extending portion 50 and outwardly extending wings 40a and 40b relative to the retainer 120.

Figure 16:
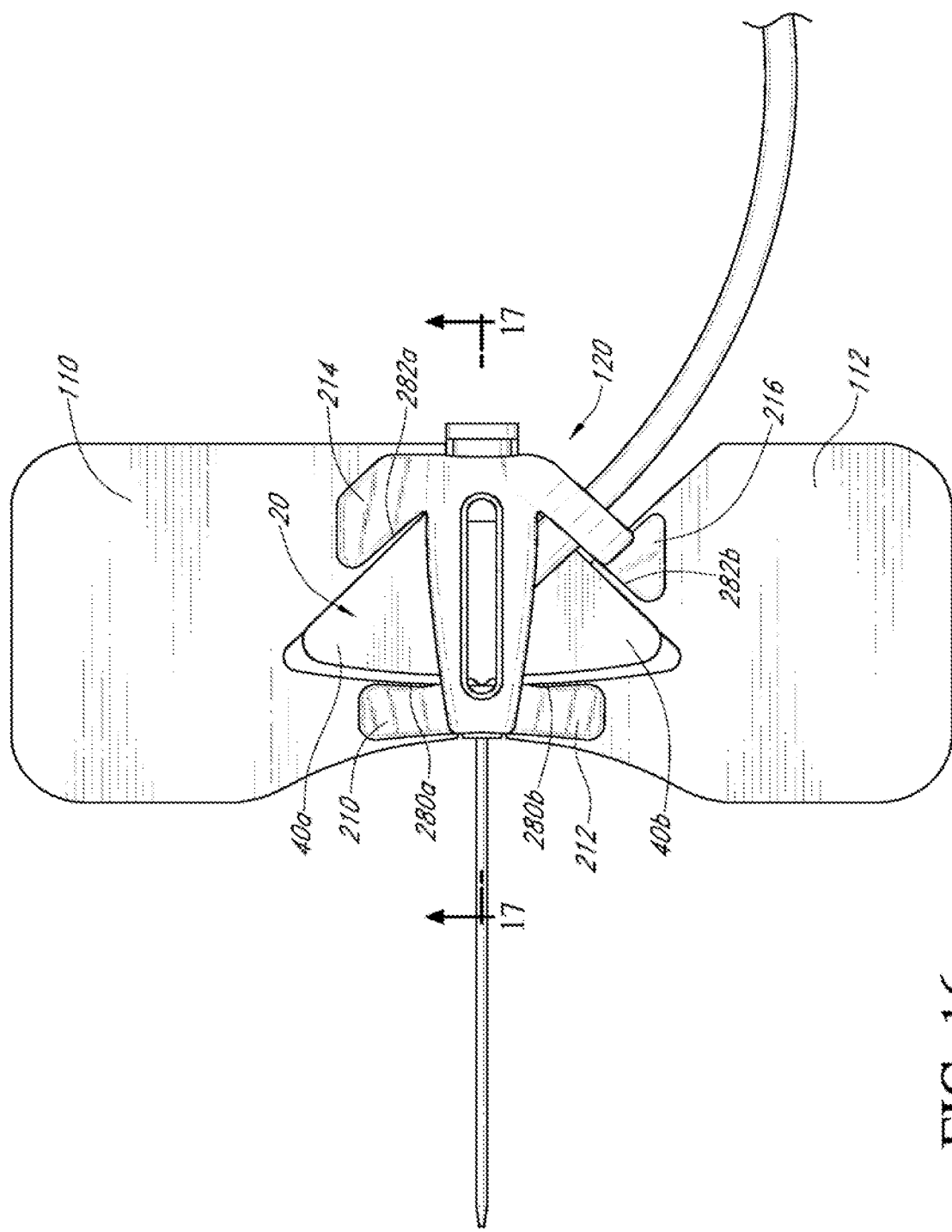
FIG. 16 is a top plan view of the securement device and medical article of FIG. 15.

FIG. 16 is a top plan view of the retainer 120 with the medical article 20 retained therein. It can be seen that the interior edges of the anchor pads 110, 112, particularly triangular cutouts 122a and 122b, cooperate with the shapes of footings 210, 212, 214, and 216 to define apertures on either side of the longitudinal axis of the retainer 120 which allow the laterally extending wings 40a and 40b of the to pass upwardly therethrough. In the illustrated embodiment, the distal edges 280a and 280b of front footings 210 and 212 are shaped to match the proximal edge of triangular cutouts 122a and 122b. Similarly, the proximal edges 282a and 282b of rear footings 214 and 216 are shaped to match the distal edge of triangular cutouts 122a and 122b.

Figure 17:
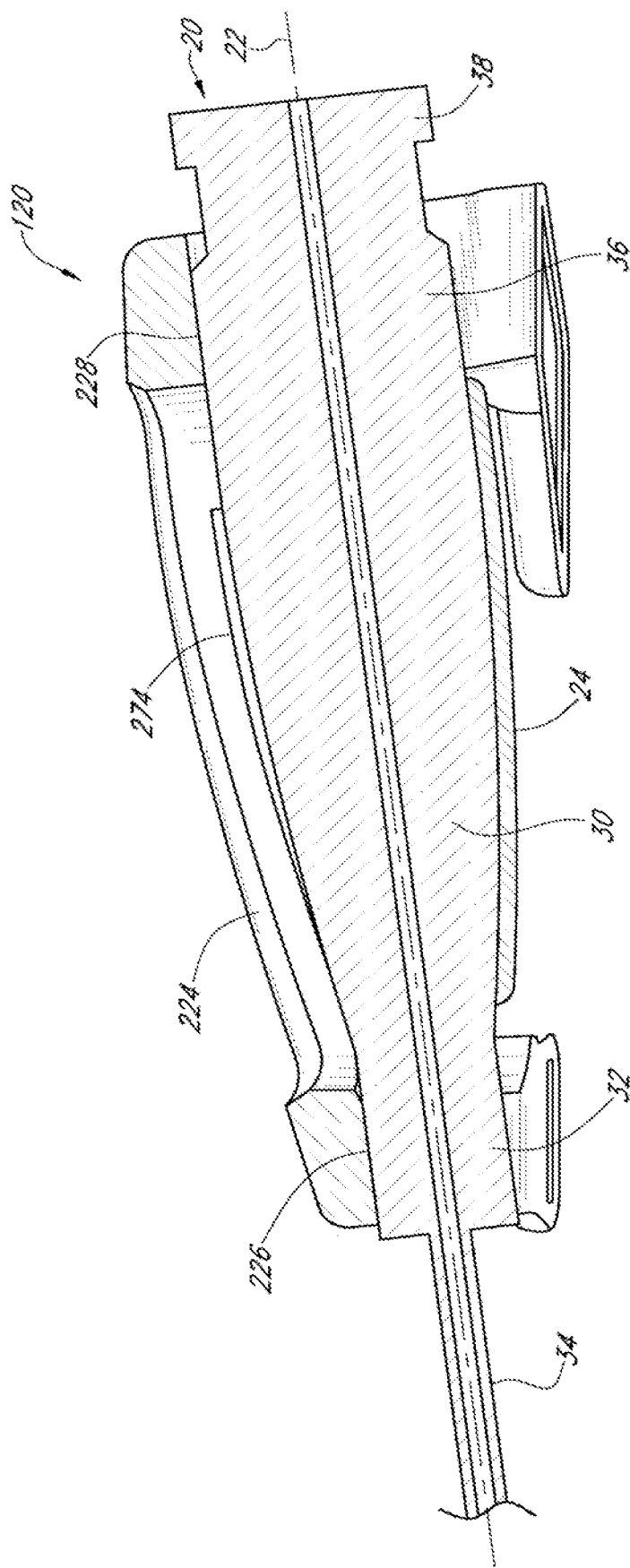
FIG. 17 is a side cross-section of the securement device and medical article taken along line 17-17 in FIG. 16.

FIG. 17 is a side cross-section of the retainer 120 with the medical device secured therein, taken along the longitudinal axis of the retainer 120. It can be seen in FIG. 17 that the medical article 20 is secured within the retainer 120 such that the longitudinal axis 22 of the medical article is aligned with the longitudinal axis of the retainer, each of which are preferably inclined at an angle to the underlying skin of the patient. A variety of different angles can be used, ranging from 0° to 45°, and more preferably from 5° to 25°. For instance, for the securement of intravenous catheters, it is desirable for the angle of incidence of the catheter to the skin of the patient to be between about 7° to about 15°. For the securement of arterial catheters, it is desirable for the angle of incident of the catheter to the skin of the patient to be about 12.5°. It can also be seen in FIG. 17 that the lower surface 24 of the retained medical article 20 will be spaced apart from the skin of the patient, such that the article itself does not come into contact with the skin of the patient.

In one embodiment, use of the securement device may proceed as follows. A proximal portion of a medical article 20 may be inserted into a patient, and a caregiver aligns the central body 30 with the securement device 100, which includes the anchor pads 110 and 112 and the retainer 120. The securement device 100 is oriented such that the proximal portion 206 and proximal abutment surface 226 overlie the front substantially cylindrical portion 32 of the medical article 20, and the distal portion 208 and distal abutment surface 228 overlie the back substantially cylindrical portion 36 of the medical article 20. The aperture 224 in the central portion 204 of the retainer 120 may serve as a viewport and facilitate this alignment.

The medical article 20 is then brought upwards between the anchor pads 110 and 112 such that the laterally extending wings 40a and 40b pass through the cutouts 122a and 122b on their interior edges. Upward pressure on the medical article 20 and the inwardly extending portions causes a slight outward deformation of the retainer, allowing the proximal and distal substantially cylindrical portions of the medical article to be pressed into and form a snap-fit configuration with the corresponding abutment surfaces.

Figure 18:
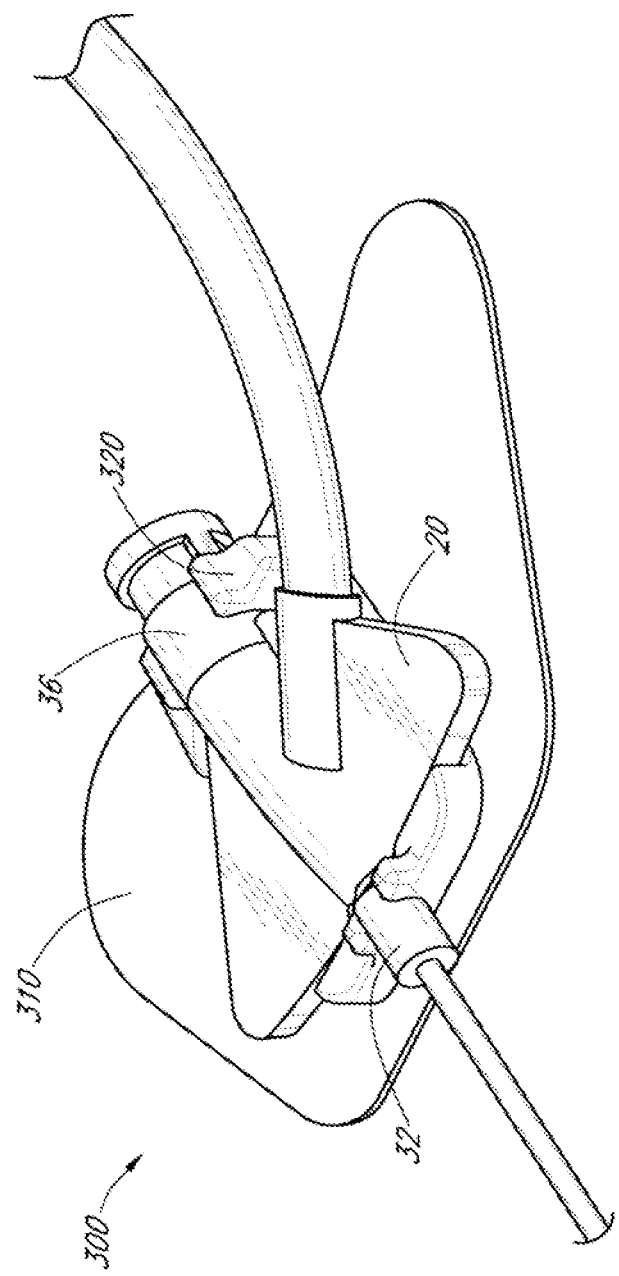
FIG. 18 is a perspective view of another embodiment of a securement device for receiving the medical article from FIG. 2.

In alternate embodiments, a medical article such as medical article 20 can be secured via a securement device having an upwardly opening channel, such that the bulk of the retainer is located between the medical article 20 and the skin of the patient when the medical article is retained therein. FIG. 18 illustrates such an embodiment of a securement system 300, in which a medical article 20 is secured within a retainer 320 disposed on a single anchor pad 310 which may be adhered to the skin 10 of a patient in a similar fashion as that illustrated in FIG. 1. It can be seen in FIG. 18 that the proximal substantially cylindrical section 32 and the distal substantially cylindrical section 36 of the medical article 20 are retained between opposing pairs of upwardly extending members in order to inhibit at least lateral motion of the medical article 20 relative to the retainer 320.

Figure 19:
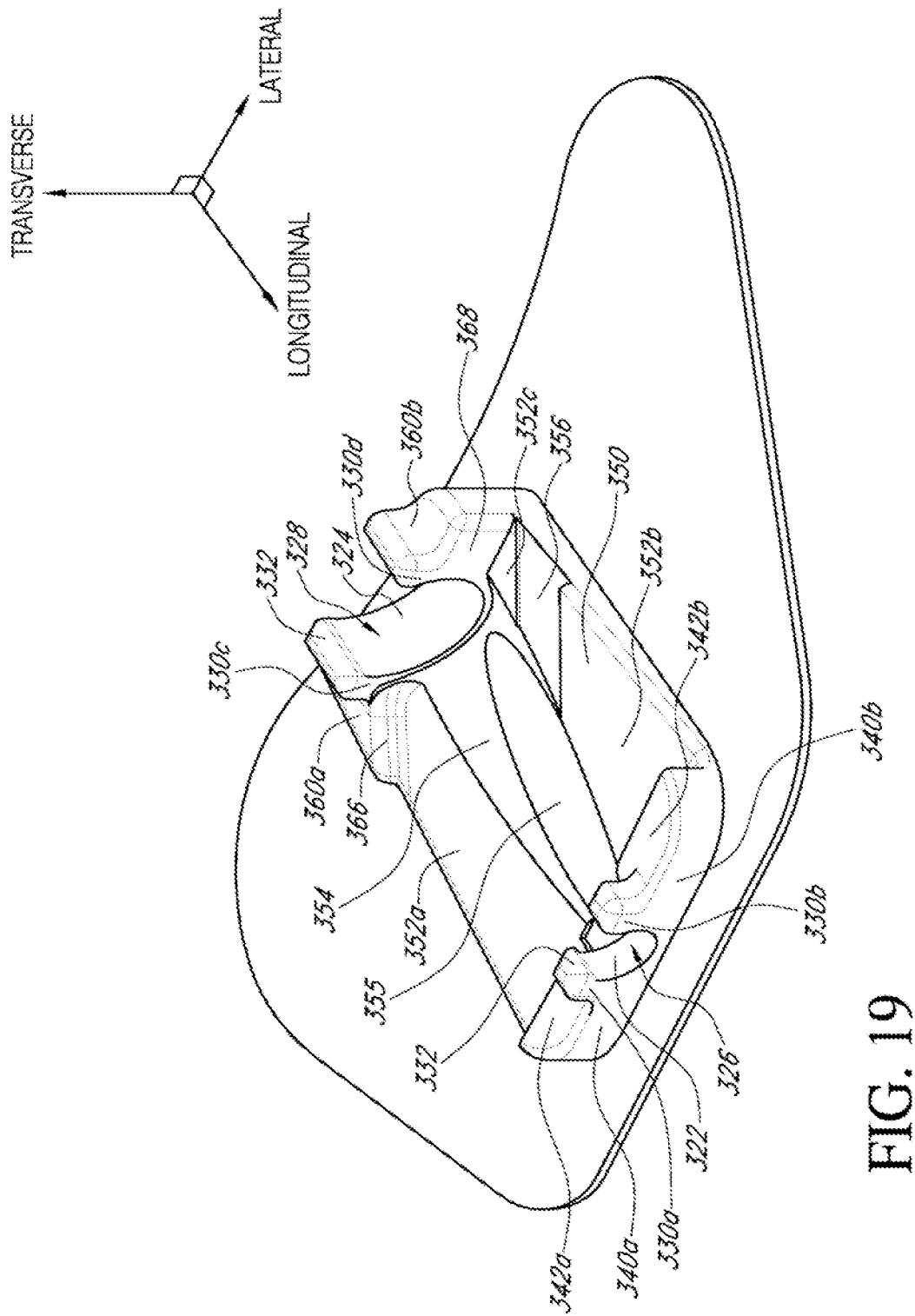
FIG. 19 is a perspective view of the securement device of FIG. 18 without the medical article.

FIGS. 19-27 illustrate various views of the retainer 320 and anchor pad 310. In FIG. 19, it can be seen that a proximal or front abutment surface 322 is defined by a substantially semicylindrical channel 326 located between a front left retention member 330a and a front right retention member 330b. Similarly, a distal or rear abutment surface 324 is defined by a substantially semicylindrical channel 328 located between a back left retention member 330c and a back right retention member 330d.

Figure 20:
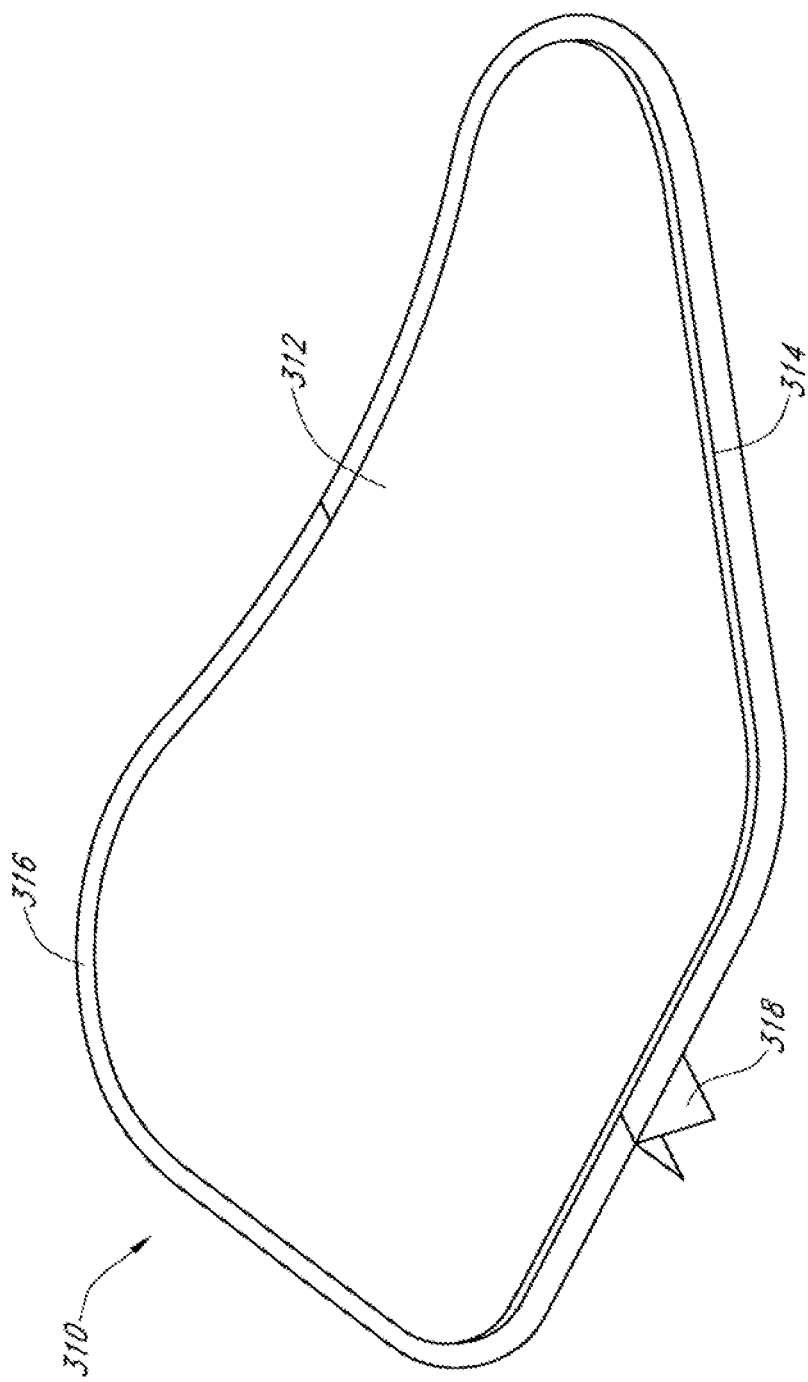
FIG. 20 is a perspective view of the anchor pad from the securement device of FIG. 19.

FIG. 20 is a perspective view of the anchor pad 310. In contrast to the anchor pads 110 and 112 of the previous embodiment, only a single anchor pad 310 is utilized in the illustrated embodiment of securement system 300. As the medical article 20 can be inserted into the retainer 320 from above, the securement system 300 does not require an aperture in the anchor pads through which the medical article is inserted. The anchor pad 310 may have a generally trapezoidal shape, and may be symmetrical about a longitudinal axis of the securement system 300, narrowing in the proximal direction. As can be seen in FIGS. 18 and 19, the anchor pad 310 may have a footprint which extends beyond not only the footprint of the retainer 320, but also beyond the edges of the laterally extending wings 40a and 40b of the medical article when retained within the securement system 300. A wide variety of other shapes and sizes of anchor pads may also be suitable for use with such a securement system.

The anchor pad 310 may be similar in other respects to the anchor pads 110 and 112 of the previous embodiment. The anchor pad 310 comprises a removable liner 316 in contact with the lower surface 314 of the anchor pad, with pull tabs 318 to facilitate removal of the anchor pad. The anchor pad 310 further comprises an upper surface 312 to which the retainer 320 can be secured.

Figure 22:
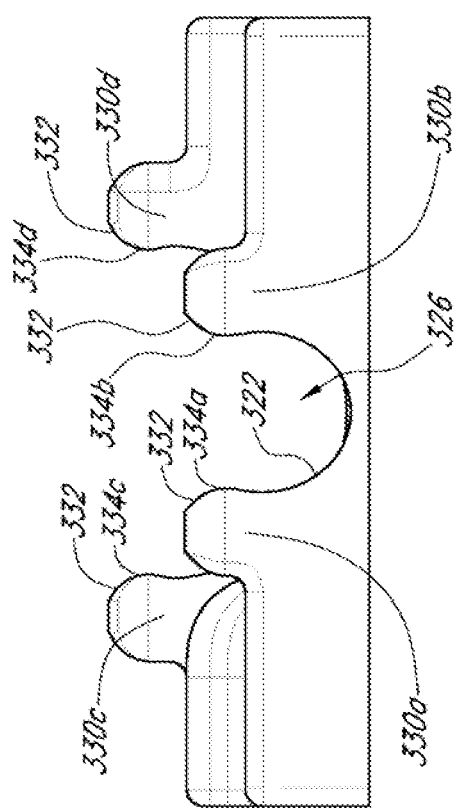
FIG. 22 is a front view of the retainer of the securement device taken along line 22-22 in FIG. 21 without the anchor pad.
Figure 23:
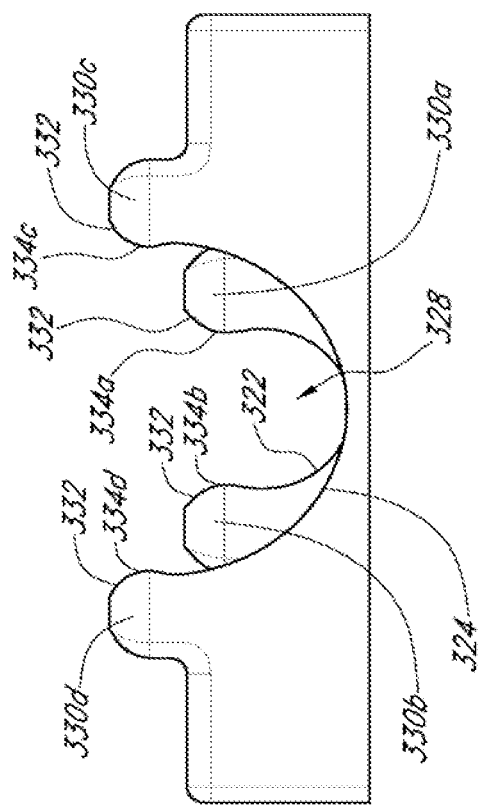
FIG. 23 is a back view of the retainer of the securement device taken along line 23-23 in FIG. 21 without the anchor pad.

As can most clearly be seen in FIGS. 22 and 23, the retention members 330a-330d comprise inwardly extending lips 334a-334d, such that the abutment surfaces 322 and 324 include the lower surfaces of these inwardly extending lips 334a-334d and the abutment surfaces 322 and 324 therefore extend slightly more than 180° around a longitudinal axis of the retainer 320. The retention members 330a-330d may comprise a resilient material or a resilient thickness of material such that some outward deformation of the retention members 330a-330d is possible. The inwardly extending lips of each pair of retention members may be spaced apart from one another by a distance which is slightly less than the diameter of the portion of the medical article to be retained by that pair of retention members, such that the retention members may be deformed outward to allow passage of the medical article 20 into the channels 326 and 328. Once the medical article is in contact with substantially the entire abutment surfaces 322 and 324, the pairs of retention members may move back towards one another, such that the inwardly extending lips may inhibit transverse motion of the medical direction. The outward deformation of the retention members 330a-330d to allow passage of the medical article 20 thereby may be facilitated by chamfered contact surfaces 332 located on the upper interior portions of the retention members 330a-330d.

Figure 21:
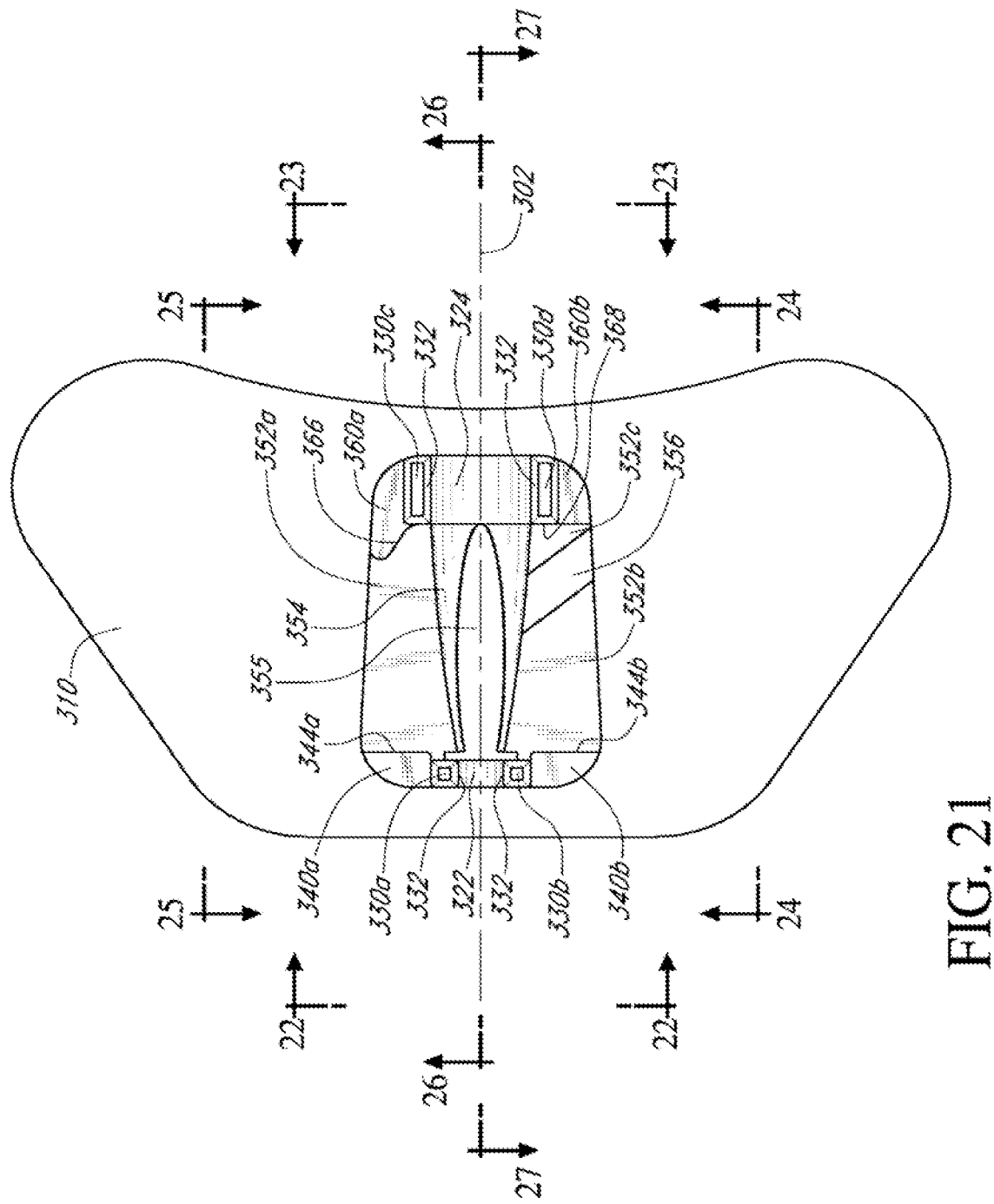
FIG. 21 is a top plan view of the securement device of FIG. 19.

With respect to FIGS. 19 and 21, it can be seen that the proximal end of the retainer 320 includes raised portions 340a and 340b, which extend upward to a height which is less than the maximum height of the retention members 330a and 330b. The raised portions 340a and 340b further comprise substantially coplanar upper surfaces 342a and 342b, as well as distal faces 344a and 344b. The distal faces 344a and 344b may extend either outward in a lateral direction, or may extend at a slight distal angle corresponding to the angle of the proximal edges of the laterally extending wings 40a and 40b of medical article 20. These distal faces may prevent longitudinal motion of a retained medical article in a proximal direction relative to the retainer 320, as the forward edges of the wings 40a and 40b will abut the distal faces 344a and 344b during such movement.

In certain embodiments, the upper surfaces 342a and 342b may rise to a height which is substantially equal to that of the upper surface of the laterally extending wings 40a and 40b of the medical article 20 when the medical article is secured within the retainer. By avoiding a significant disparity in the height of the front edge of the laterally extending wings and the raised portions 340a and 340b, no edge is provided on which another object could catch and cause dislodgement of the medical article or other distress to the securement device or insertion site. In further embodiments, the upper surfaces 342a and 342b may be oriented at a slight angle, equal to the incline of the longitudinal axis 302 of the retainer 320, such that the upper surface of the wings 40a and 40b and the upper surfaces 342a and 342b may be substantially coplanar. In other embodiments, however, the upper surfaces 342a and 342b may rise to a height which is greater or less than the height of the front edge of the wings 40a and 40b.

As can be seen in FIGS. 19 and 21, the distal end of the retainer 320 includes raised left rear portion 360a and raised right rear portion 360b. In contrast to the raised front portions 340a and 340b, the raised rear portions 360a and 360b are not symmetrical. The raised left portion 360a, which will be located on the opposite side of the medical article 20 from the outwardly extending portion 50 and tubing 52 of the medical article 20, includes a proximal face 366 which is shaped to be substantially complimentary to that of the left laterally extending wing, including a curved interior section and located closer to the longitudinal axis 302 of the retainer 320 than a linearly extending outer section which extends at an angle substantially corresponding to the angle of the rear edge of the linearly extending wing. In contrast, the proximal face 368 of the raised right rear portion 360b extends laterally outward without extending longitudinally forward, so as to allow passage thereby of the outwardly extending member 50 and associated tubing 52 of the medical article 20 without interference.

A base 350 of the retainer 320 extends generally between the raised portions located at the proximal and distal ends of the retainer. Upper surfaces 352a, 352b, and 352c of the base are generally coplanar and oriented parallel to the longitudinal axis 302 of the retainer 320. A longitudinally extending central channel 354 runs through the center of the base, and is dimensioned to allow the central body 30 of the medical article to be retained therein. In certain embodiments, a generally elliptical aperture 355 located at the base of the channel 354 may allow a portion of a retained medical article to come into contact with the underlying anchor pad 310. A side channel 356 extends outward from the central channel 354 and is oriented at an angle to the longitudinal axis 302 of the retainer 320 which corresponds to the angle of the outwardly extending member 50 of the medical article 20. The depth of the side channel 356 may be less than the depth of the central channel 354, given the relative thicknesses of the central body 30 and the outwardly extending member 50 of the medical article 20.

Thus, in certain embodiments, some or all of the planar upper surfaces 352a-352c, the channel 356, and the channel 354 may serve as abutment surfaces to constrain movement of the medical article 20. In particular, the planar surfaces 352a-352c may prevent rotation of the medical article about the longitudinal axis, as rotation of the article may bring the lower surfaces of wings 40a or 40b into contact with planar surfaces 352a-352c. If the depth of side channel 356 is substantially equal to or less than the height differential between the base of the wing 40b and the base of the outwardly extending member 50 extending therethrough, the base of channel 356 may also serve as an abutment surface to prevent rotation. Similarly, any of surfaces 352a-352c, the channel 356, and the channel 354 may serve as an abutment surface to inhibit excessive downward flexure of portions of the medical article 20.

Operation of the securement device 300 may proceed as follows: A liner 316 may be removed to expose the lower surface 314 of an anchor pad 310, and the anchor pad 310, with a retainer 320 fixed thereon, may be adhered to the skin of a patient. A medical article 20 may be positioned over the retainer 320 such that a substantially cylindrical front section 32 overlies a proximal abutment surface 322 and a substantially cylindrical back section 36 overlies a distal abutment surface 324. The medical article is then pressed downward, and the interaction between the curved underside of the substantially cylindrical sections causes the front pair of retention members 330a and 330b and the back pair of retention members 330c and 330d to deform slightly outward in a lateral direction from the other retention member in the pair, allowing the substantially cylindrical sections to be brought into contact with the proximal and distal abutment surfaces. The retention members then flex back inward so as to slightly overlie portions of the medical article to prevent transverse movement of the medical article relative to the retainer. Further movement of the medical article is inhibited by the various abutment surfaces as described above.

Figure 24:
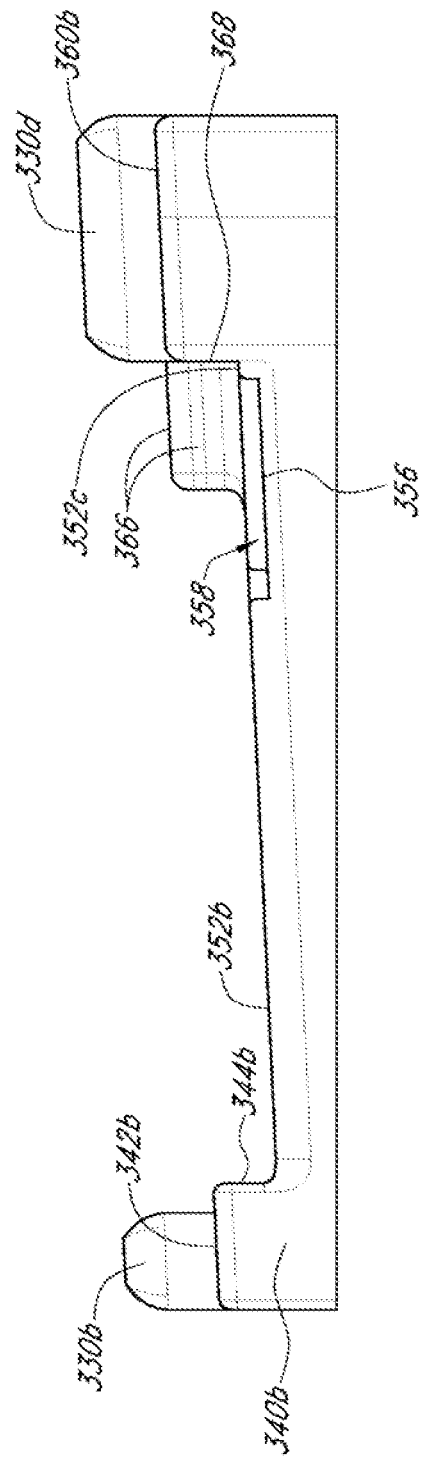
FIG. 24 is a right side view of the retainer of the securement device taken along line 24-24 in FIG. 21 without the anchor pad.
Figure 25:
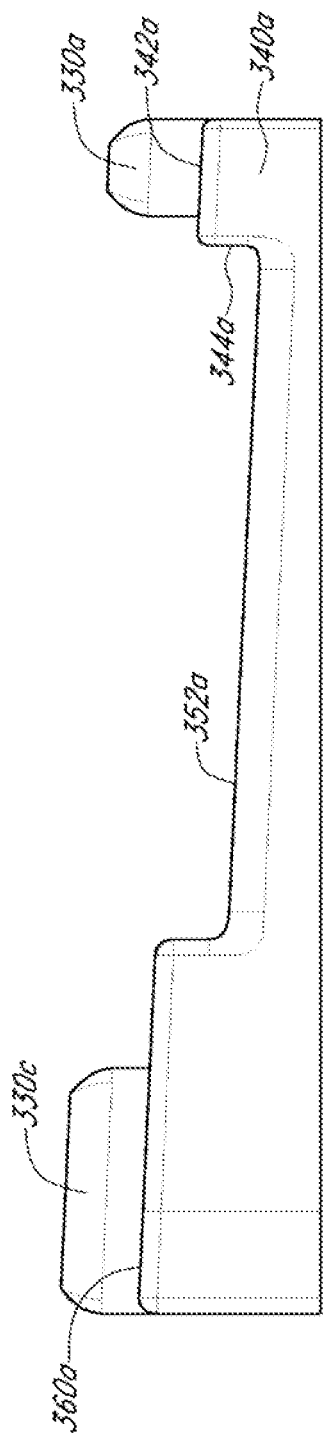
FIG. 25 is a right side view of the retainer of the securement device taken along line 25-25 in FIG. 21 without the anchor pad.

FIG. 24 is a right side view of the retainer of the securement device taken along line 24-24 in FIG. 21 without the anchor pad. FIG. 25 is a right side view of the retainer of the securement device taken along line 25-25 in FIG. 21 without the anchor pad. In FIGS. 24 and 25, the angles of upper surfaces 352a and 352b of the base are visible. It can also be seen that in the illustrated embodiment, the surfaces 342a, 342b, 360a and 360b are substantially parallel to and transversely offset from surface 352b. This configuration enables the upper surfaces of wings 40a and 40b of the medical article to lie substantially parallel to and aligned with the surfaces 342a, 342b, 360a and 360b in particular embodiments.

Figure 26:
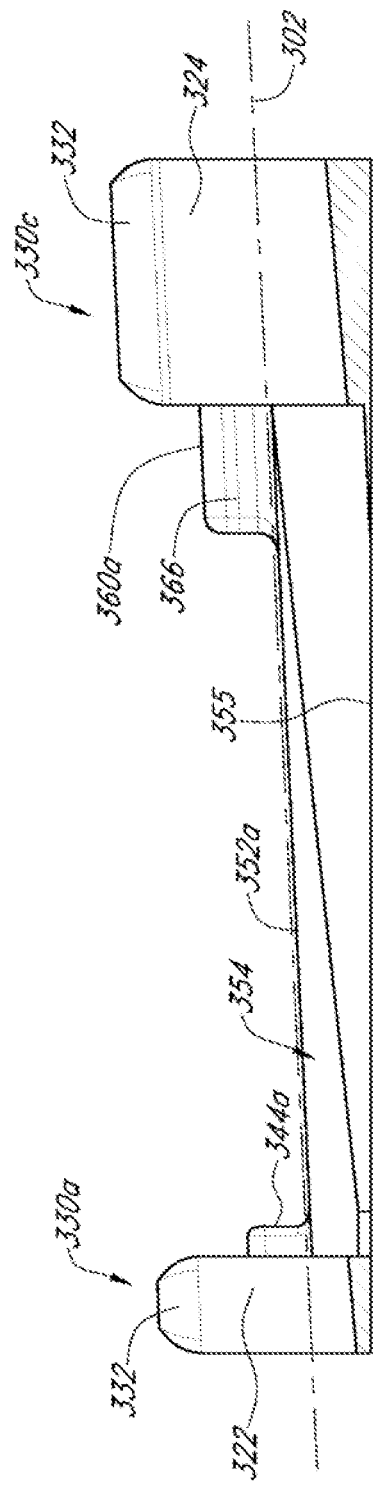
FIG. 26 is a cross-section view of the retainer taken along line 26-26 in FIG. 21 without the anchor pad.
Figure 27:
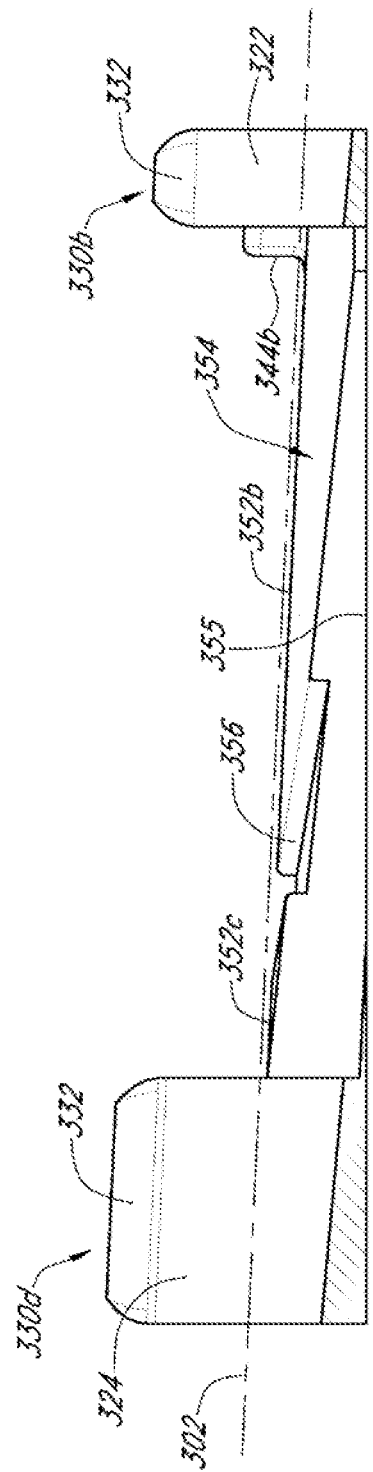
FIG. 27 is a cross-section view of the retainer taken along line 27-27 in FIG. 21 without the anchor pad.

FIG. 26 is a cross-section view of the retainer taken along line 26-26 in FIG. 21 without the anchor pad. FIG. 27 is a cross-section view of the retainer taken along line 27-27 in FIG. 21 without the anchor pad. In FIGS. 26 and 27, it can be seen that the upper surfaces 352a and 352b of the base are substantially parallel to the longitudinal axis 302 of the retainer.

Figure 28:
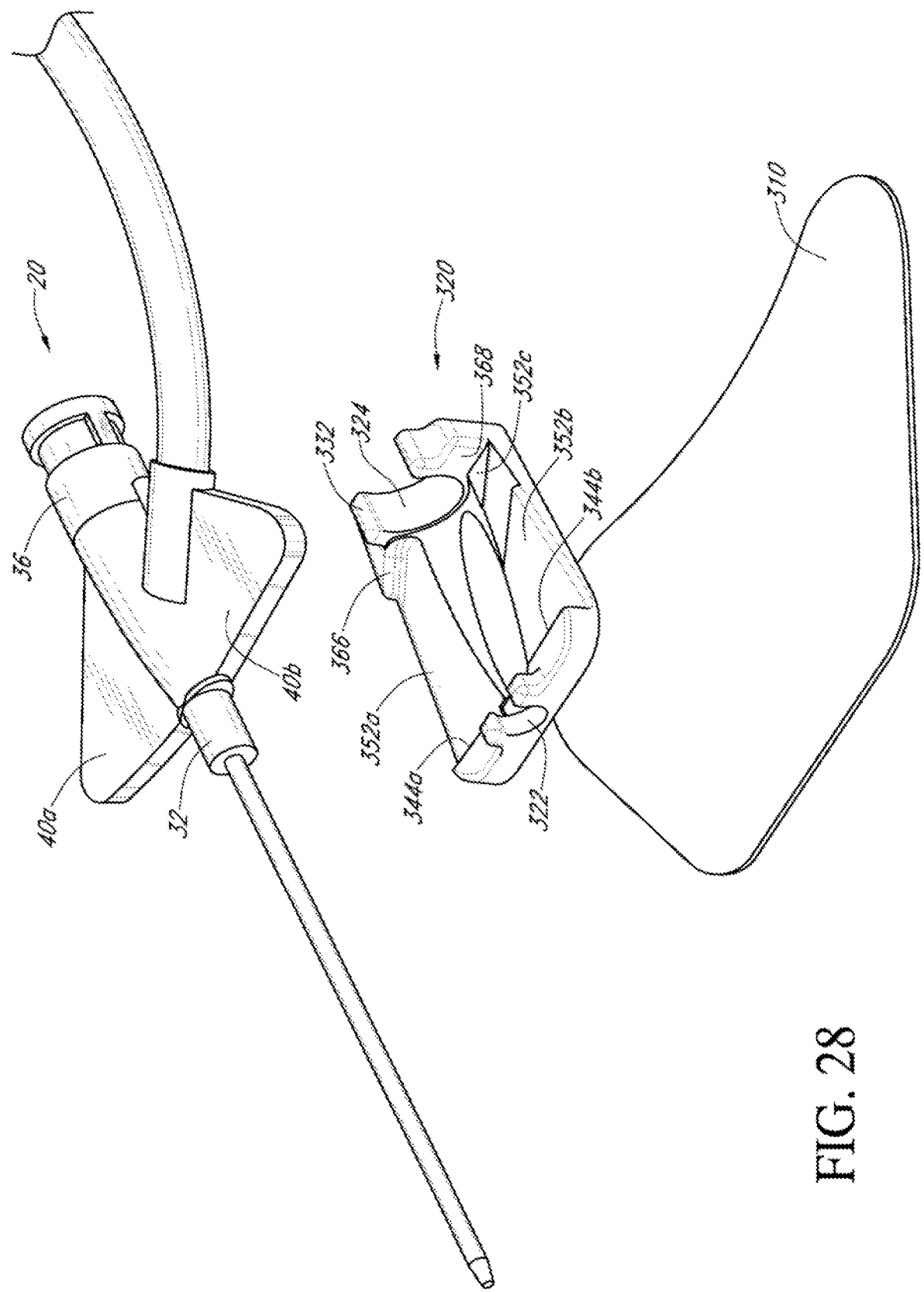
FIG. 28 is an exploded assembly view of the securement device and medical article of FIG. 18.

FIG. 28 is an exploded assembly view of the securement device and medical article of FIG. 18. It can be seen in FIG. 28 that the side channel 356 may provide both tactile and visual guidance to a caregiver regarding the desired longitudinal position of the medical article 20 relative to the retainer. The proximal face 366 of the raised left portion 360a and the distal faces 344a and 344b of the front raised portions 340a and 340b may also provide such guidance.

Figure 29:
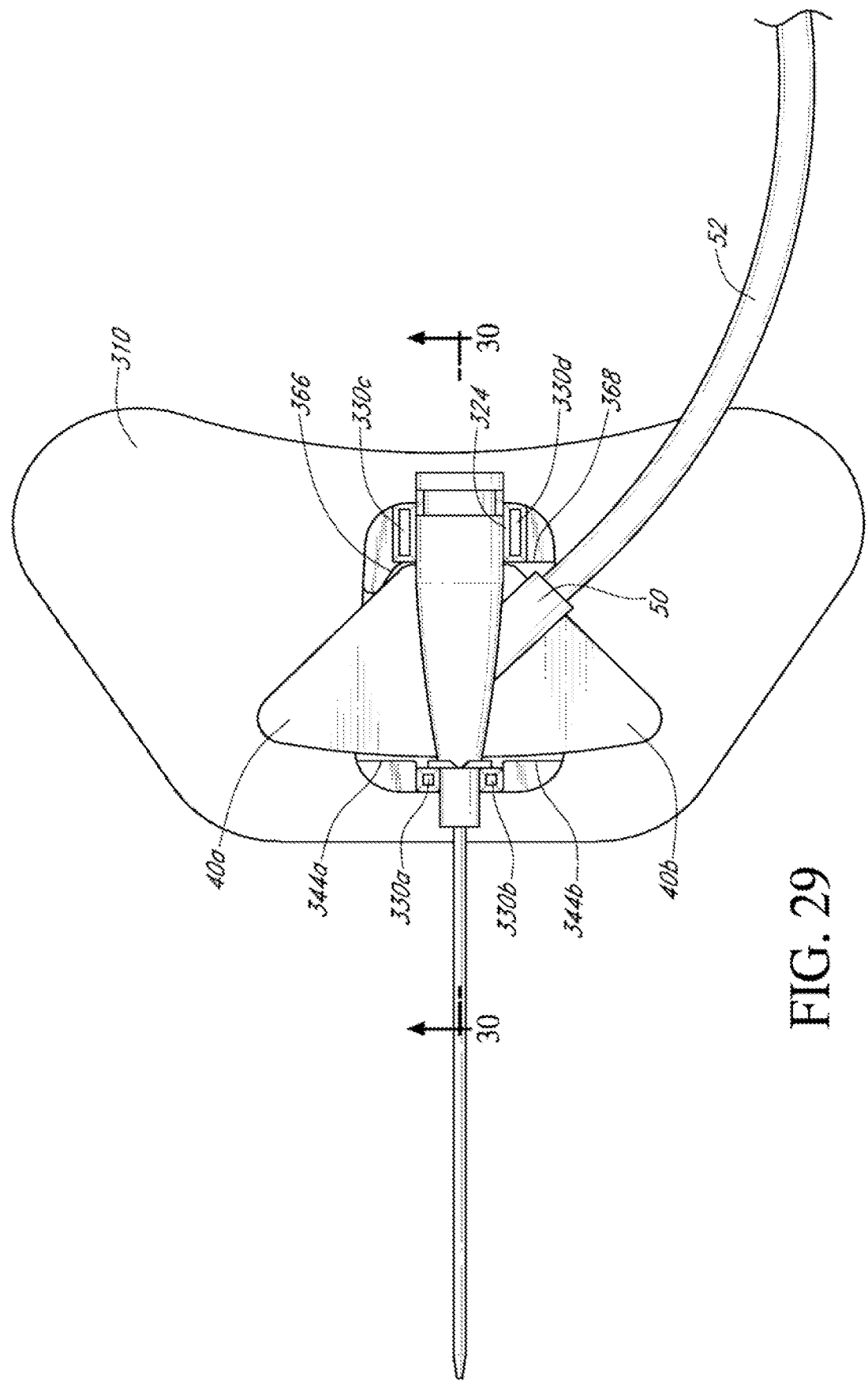
FIG. 29 is a top plan view of the securement device of FIG. 18 with the medical article retained therein.

FIG. 29 is a top plan view of the retainer 320 with the medical article 20 retained therein. It can be seen that the distal edges 344a and 344b of raised proximal portions 340a and 340b along with proximal edge 366 of raised distal portion 360a cooperate to define a receiving space which is substantially complimentary to the footprint of the medical article 20, and in particular to the shape of the laterally extending wings 40a and 40b.

Figure 30:
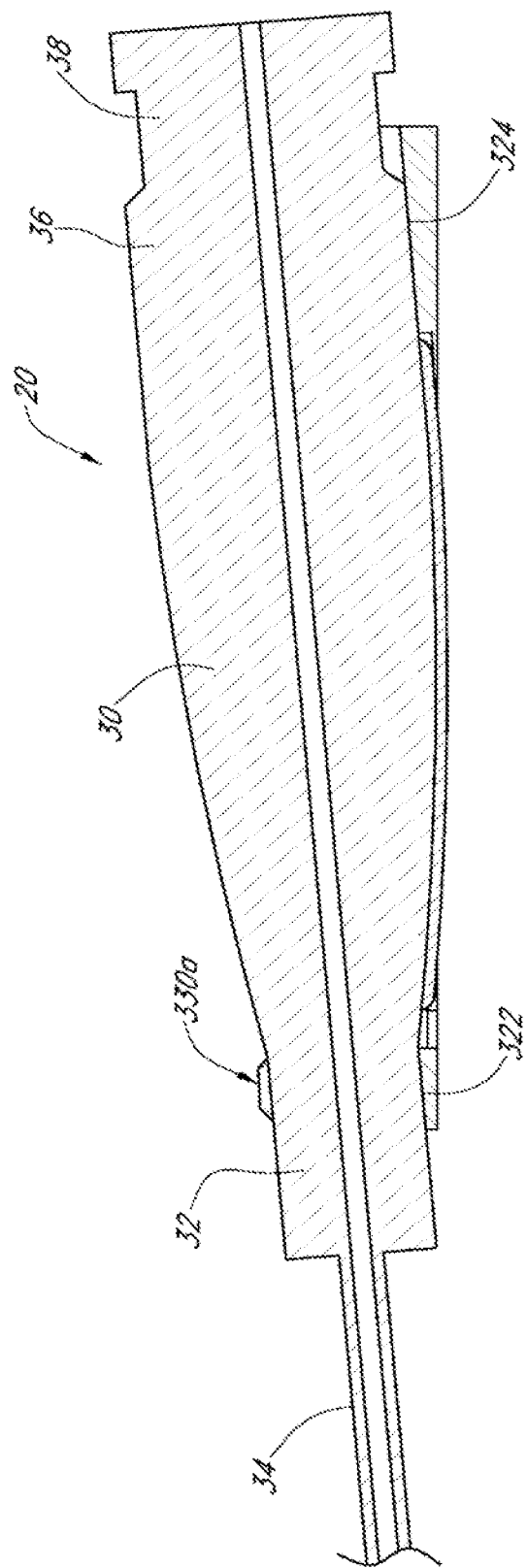
FIG. 30 is a cross-section view of the retainer taken along line 30-30 in FIG. 29 without the anchor pad.

FIG. 30 is a side cross-section of the retainer 320 with the medical device 20 secured therein, taken along the longitudinal axis of the retainer 320. It can be seen in FIG. 30 that the medical article 20 is secured within the retainer 320 such that the longitudinal axis 22 of the medical article is aligned with the longitudinal axis of the retainer 320, each of which are preferably inclined at an angle to the underlying skin of the patient. As noted above with respect to the previous embodiment, a variety of different angles can be used, ranging from 0° to 45°, and more preferably from 5° to 25°.

Figure 31:
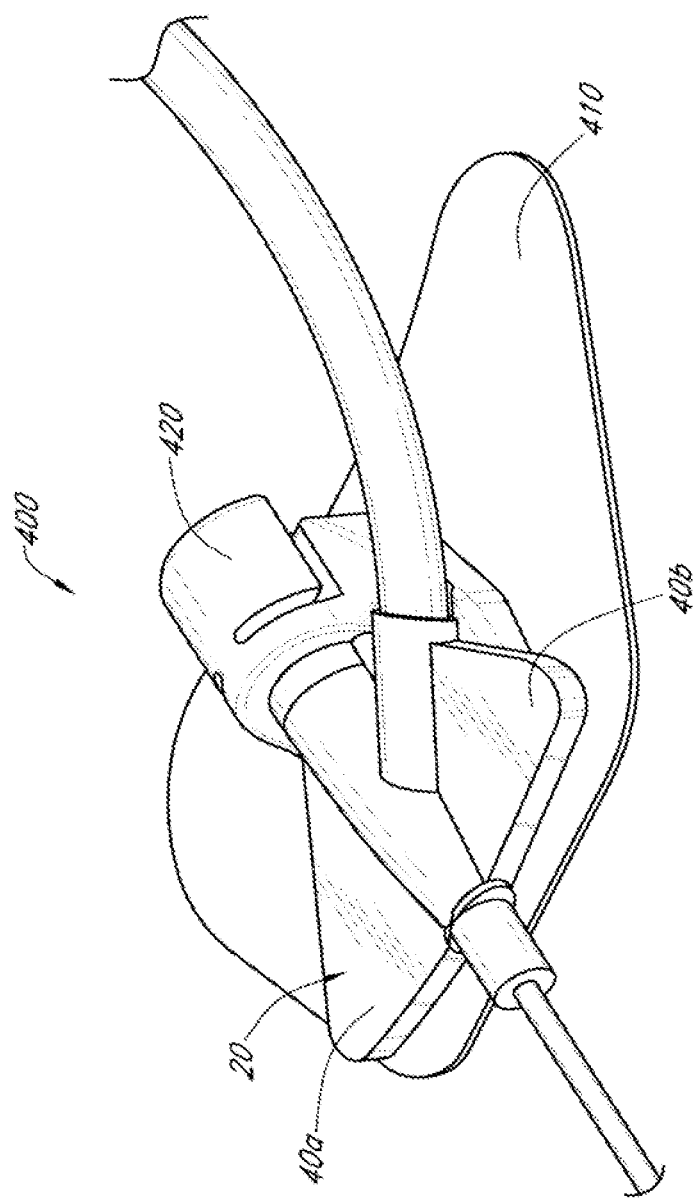
FIG. 31 is a perspective view of another embodiment of a securement device for receiving the medical article from FIG. 2.
Figure 32:
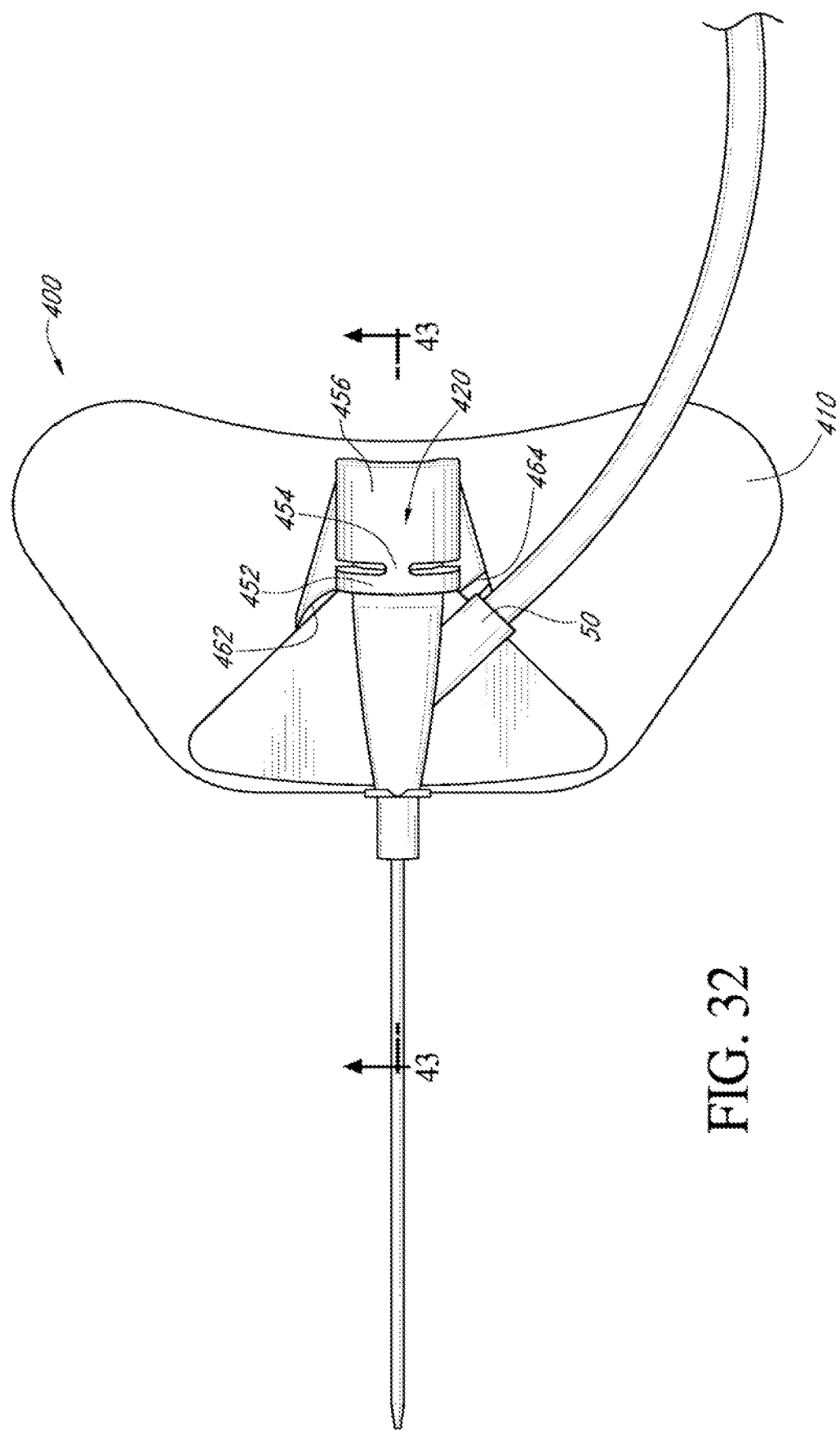
FIG. 32 is a top plan view of the securement device and retained medical article of FIG. 31.

FIG. 31 illustrates another embodiment of a securement device 400, which comprises a retainer 420 disposed on an anchor pad 410. FIG. 31 is a perspective view of the retainer 420 and the anchor pad 410. FIG. 32 is a top plan view of the securement device 400 and retained medical article 20 of FIG. 31.

Figure 33:
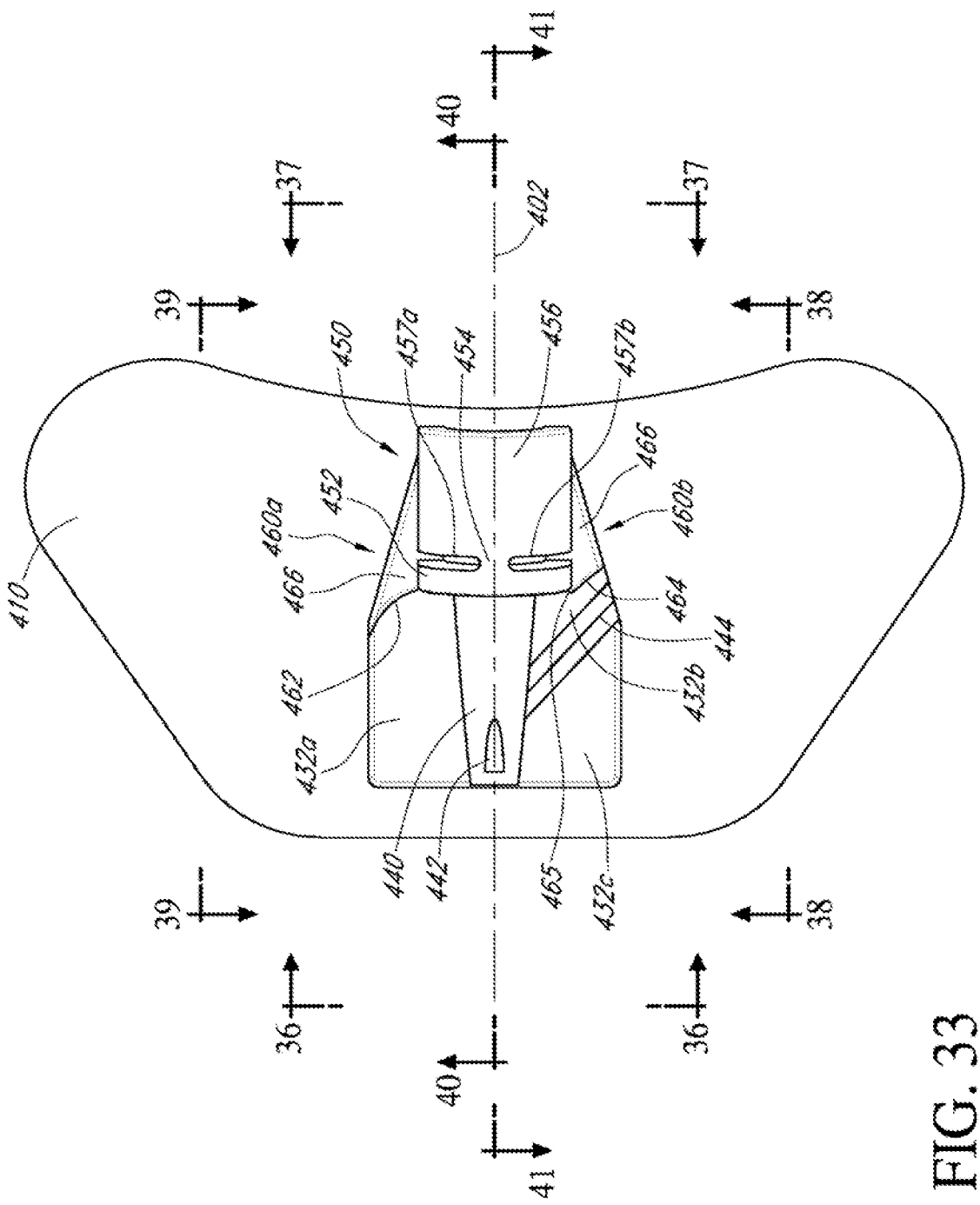
FIG. 33 is the same view as FIG. 32 except with the medical article removed.
Figure 34:
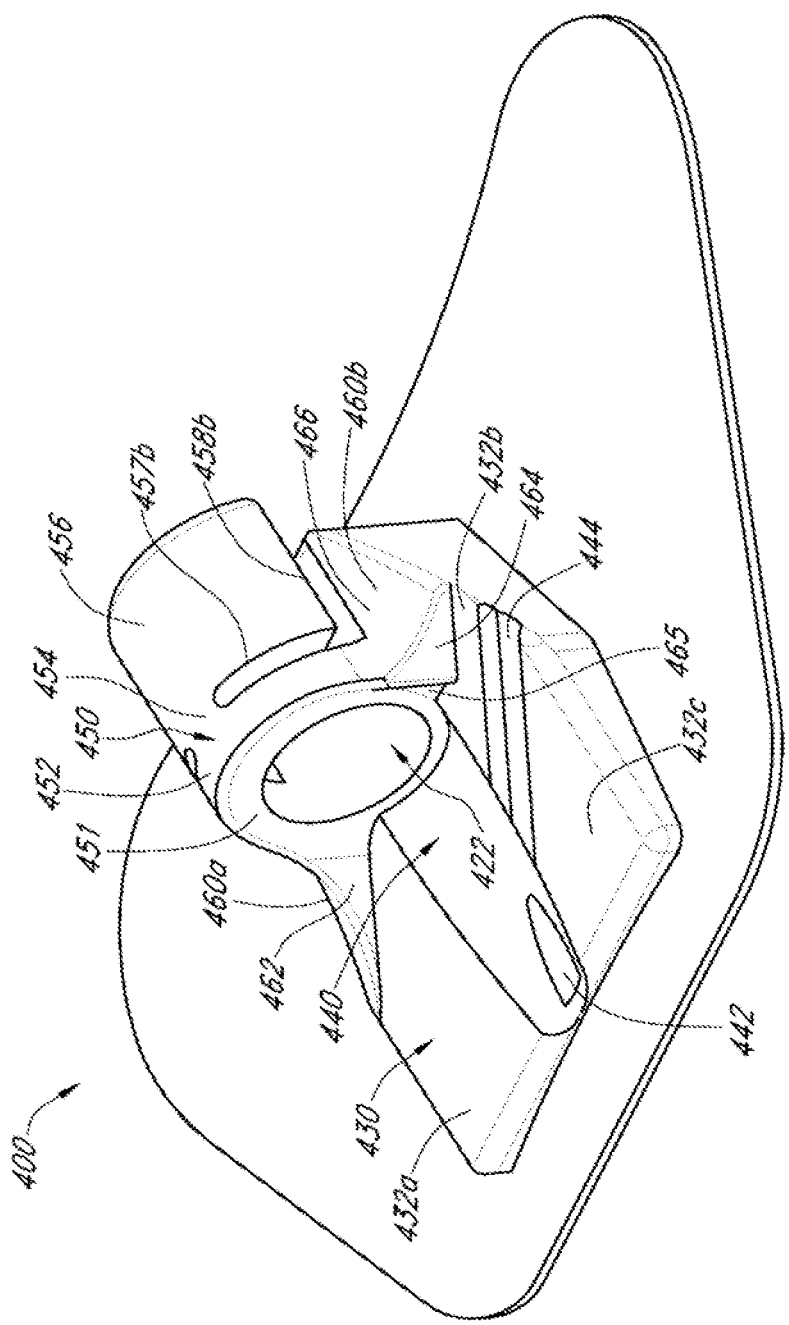
FIG. 34 is a perspective view of the securement device of FIG. 33.
Figure 35:
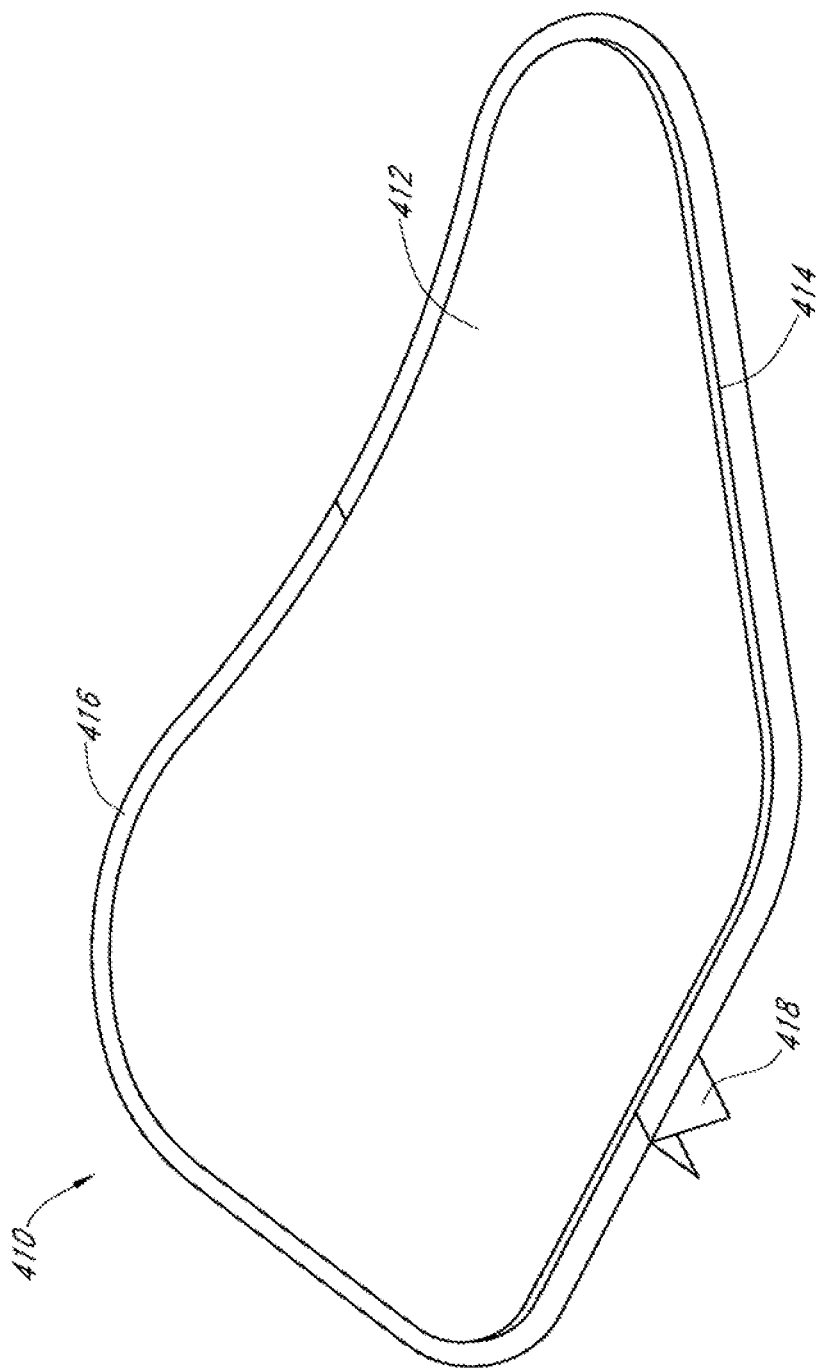
FIG. 35 is a perspective view of the anchor pad from FIG. 34.

FIGS. 33-38 illustrate various views of the retainer 420 and anchor pad 410. FIG. 35 is a perspective view of the anchor pad 410 of the securement device 400 of FIG. 31. The anchor pad 410 may be similar in size and structure to the anchor pad 310 of FIG. 20, and may include a removable liner 416 covering the bottom surface 414 of the anchor pad 410. The removable liner may comprise pull tabs 418 to facilitate removal of the liner 416. The upper surface 412 of the anchor pad 410 may be roughened or otherwise altered to facilitate fixation of the retainer 420 to the upper surface 412 of the anchor pad 410.

In FIG. 34, it can be seen that the retainer 420 comprises an angled base 430 in the proximal section of the retainer, having substantially coplanar upper surfaces 432a, 432b, and 432c. As discussed with respect to securement structure 300, these upper surfaces may be oriented at an angle substantially parallel to the angle of the longitudinal axis 402 of retainer 420, and this angle may vary based on the intended use of the medical article 20 to be retained. As discussed above, a variety of different angles can be used, ranging from 0° to 45°, and more preferably from 5° to 25°

A longitudinally extending channel 440 extends longitudinally along the base from the proximal edge of the retainer to a point at or close to the retention structure 450 at the distal end of the retainer. The channel 440 may include an aperture 442 at the base of the channel 440 if the desired depth of the channel is greater than the thickness of the base 430 at any point along the base of the channel 440. A side channel 444 extends from the longitudinally extending channel 440 to the right edge of the retainer 420, at an angle which is substantially equal to the angle at which the outwardly extending member 50 of the medical article extends. In the illustrated embodiment, the height differential between the base of the angled side channel 444 and the planar upper surfaces 432b and 432c of base 430 is substantially equal to the height differential between the base of the outwardly extending member 50 and the laterally extending wing 40b through which it extends.

The retention structure 450 comprises a channel 422 which is substantially cylindrical in shape and is centered along the longitudinal axis 402 of the retainer. The proximal end of the channel 422 is defined by a cylindrical portion extending about the longitudinal axis 402 of the retainer. The proximal interior edge 451 of the cylindrical portion 452 may be rounded or chamfered to facilitate insertion of the distal end of the medical article therein, as discussed in greater detail below.

Distal of the cylindrical portion 452, a pair of radial cuts 457a and 457b extend from points near the uppermost portion of the channel through almost a 90° arc, and ending near the midpoint of the channel. A pair of longitudinal cuts 458a and 458b extend in a distal direction from the lower ends of the radial cuts 457a and 457b and run to the proximal edge of the retention structure 450. These cuts separate an upper portion of the material defining the cylindrical channel 422 from the underlying material to form a rounded flap 456, and the portion of the retention structure 450 located between the upper ends of the radial cuts 457a and 457b serves as a connector 454 between the flap 456 and the fixed cylindrical portion 452. The thickness and/or width of the material forming the connector 454 allows resilient deformation of the flap 456 in an upwards or downwards rotation about the connector 454 while biasing the flap to return to the position illustrated in FIGS. 33, 34, and 36-38. In alternate embodiments, as discussed above, the flap 456 may be biased to return to a position in which the flap 456 is bent slightly downward towards the underlying base of channel 422.

Tapered footings 460a and 460b are located on either side of the retention structure. Each of tapered footings 460a and 460b have an curved upper surface 466 which tapers generally upward to the retention structure 450 and to the longitudinally extending cuts 458a and 458b therein to facilitate grasping of the flap 456 by a caregiver. The left tapered footing 460a has a proximal face 462 which extends away from the central channel 422 and towards the proximal edge of the retainer 420. The outer portion of the proximal face 462 of tapered footing 460a extends at an angle corresponding to the angle of the distal edge of wing 40a of the medical device 20. This proximal face 462 can thus serve as an abutment surface to interact with wing 40a to inhibit movement of a retained medical article 20 in a distal direction relative to the retainer 420. The right tapered footing 460b has a proximal face 464 which extends laterally outward and longitudinally rearward at an angle which corresponds to the angle at which the outwardly extending member 50 of the medical device 20 extends, so as to allow passage of the outwardly extending member 50 thereby when the medical article 20 is secured within the retainer 420. The right tapered footing 460b also includes an interior proximal face 465 which may serve as an abutment surface to interact with the innermost part of the distal edge of wing 40b.

Figure 36:
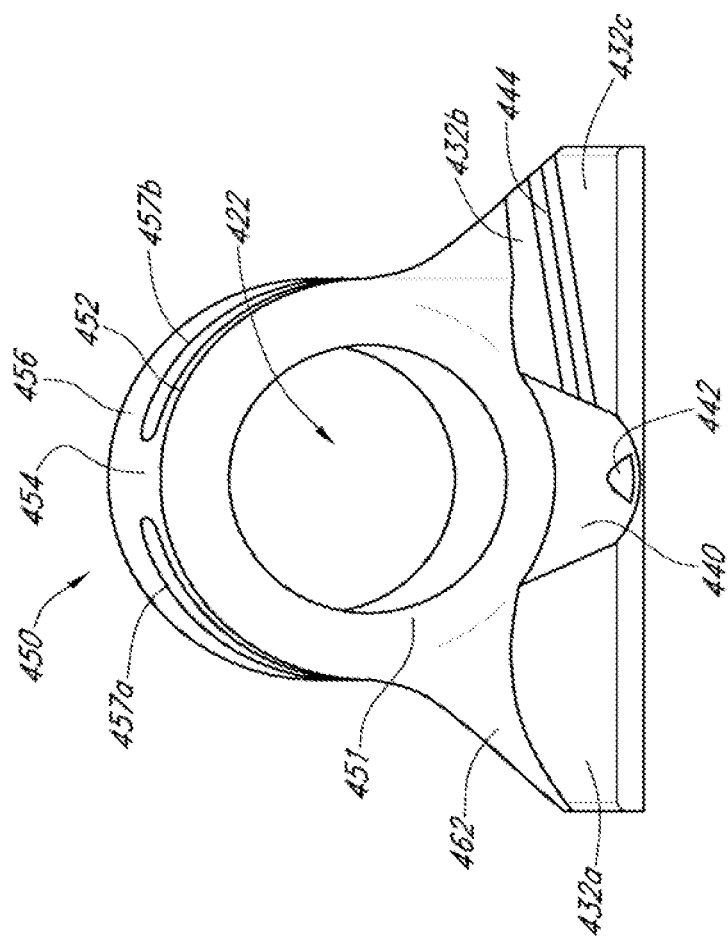
FIG. 36 is a front view of the retainer taken along line 36-36 in FIG. 33 without the anchor pad.
Figure 37:
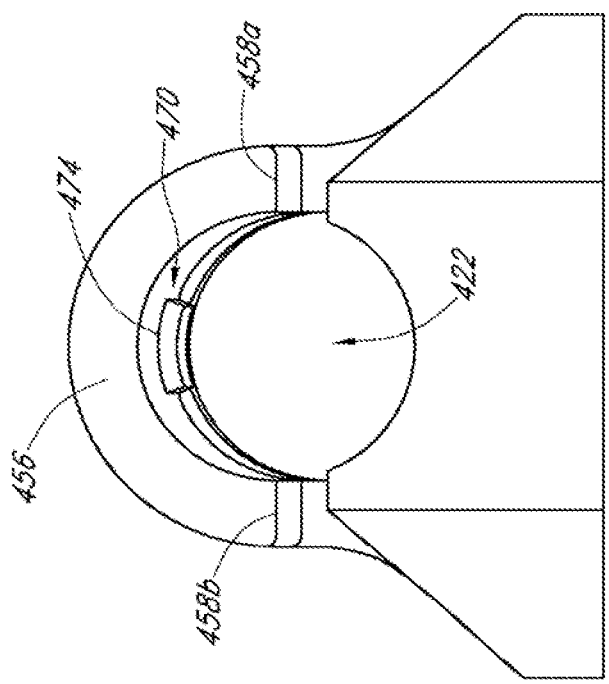
FIG. 37 is a back view of the retainer taken along line 37-37 in FIG. 33 without the anchor pad.

FIG. 36 is a front view of the retainer taken along line 36-36 in FIG. 33 without the anchor pad. FIG. 37 is a back view of the retainer taken along line 37-37 in FIG. 33 without the anchor pad. It can be seen in FIGS. 36 and 37 that the central channel 422 is substantially cylindrical and canted downward in a proximal direction. It can also be seen in FIG. 37 that the channel includes an inwardly extending tang 470 extending transversely downwards from the flap 456, which is discussed in greater detail below.

Figure 38:
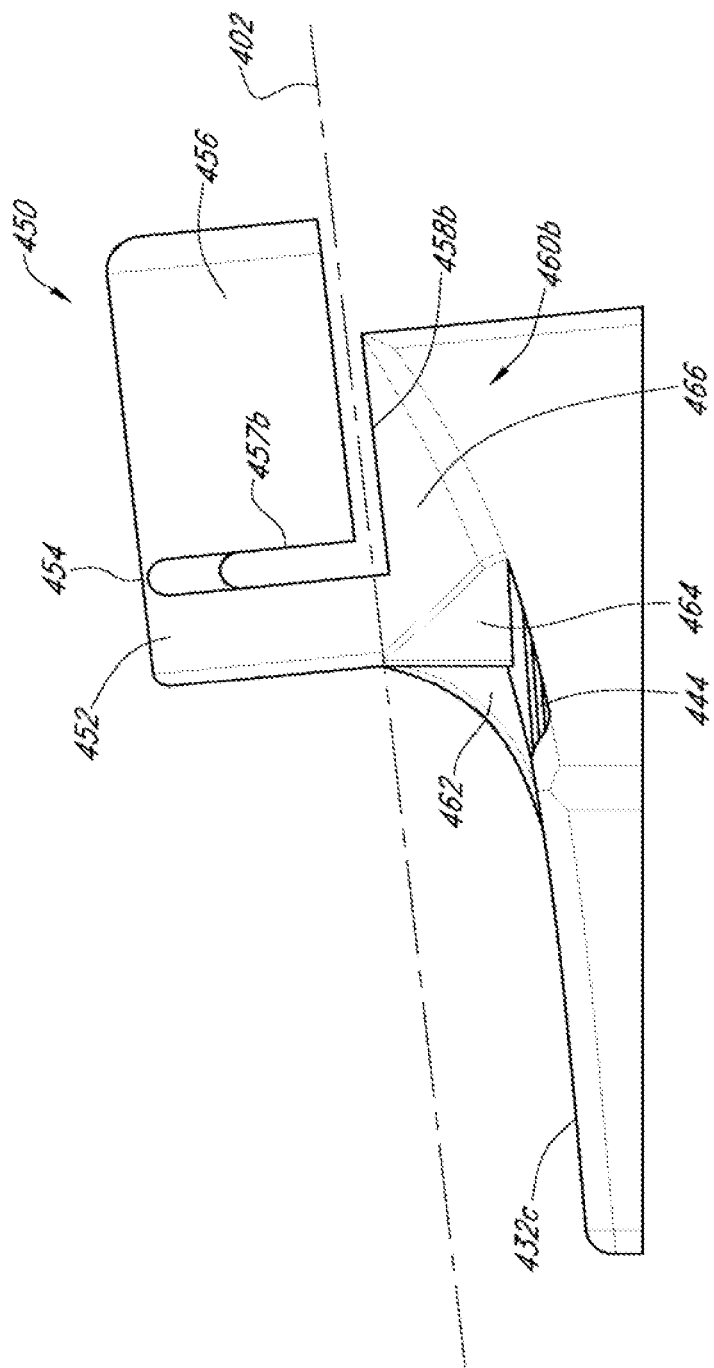
FIG. 38 is a side view of the retainer taken along line 38-38 in FIG. 33 without the anchor pad.
Figure 39:
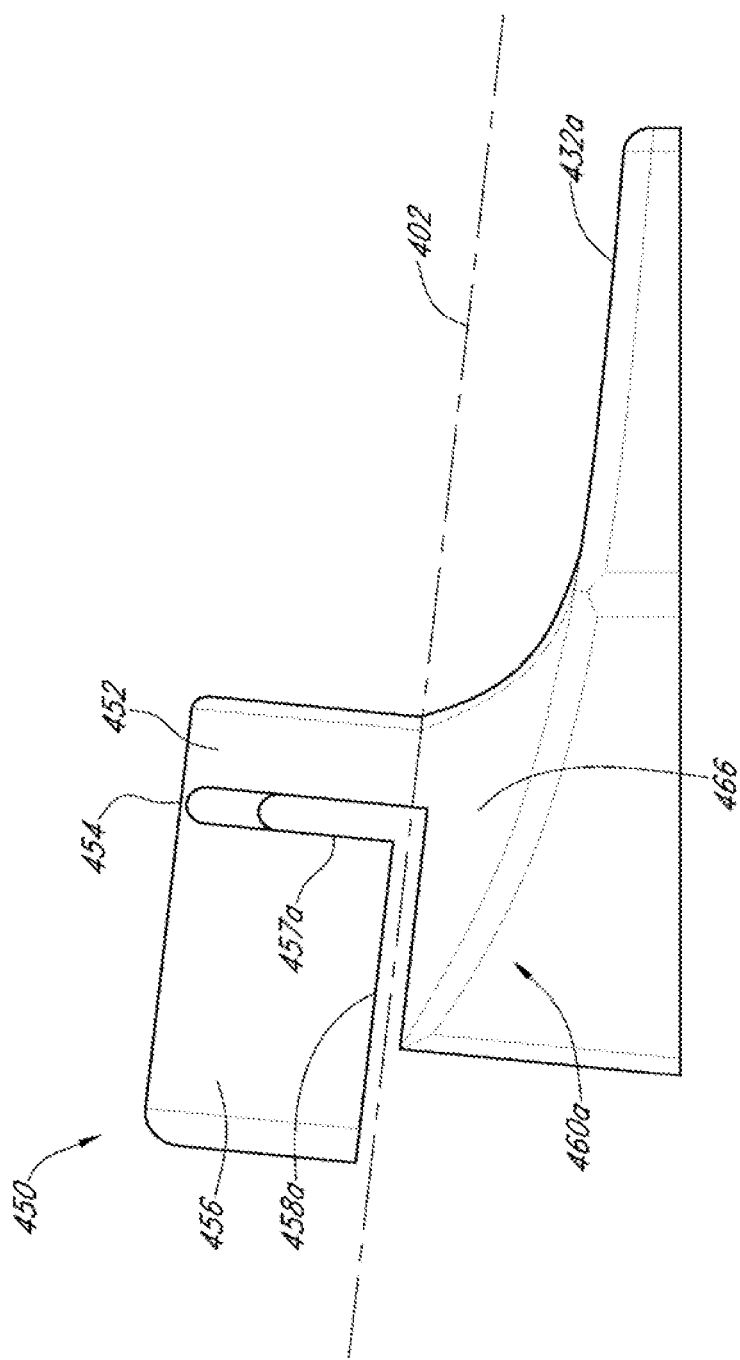
FIG. 39 is a side view of the retainer taken along line 39-39 in FIG. 33 without the anchor pad.

FIG. 38 is a side view of the retainer taken along line 38-38 in FIG. 33 without the anchor pad. FIG. 39 is a side view of the retainer taken along line 39-39 in FIG. 33 without the anchor pad. As can be seen in FIGS. 38 and 39, the longitudinally extending cuts 458a and 458b extend in a direction substantially orthogonal to a plane defined by the radial cuts 457a and 457b. In certain embodiments, however, the flap may be biased slightly downward, and the lower surface of flap 456 may contact the underlying surface at the distal end of the retainer when no medical article is retained therein. It can also be seen in FIGS. 38 and 39 that the upper surfaces 432a and 432c of base 430 slope downward in a proximal direction and are oriented at an angle substantially parallel to that of the longitudinal axis 402 of the retainer.

Figure 40:
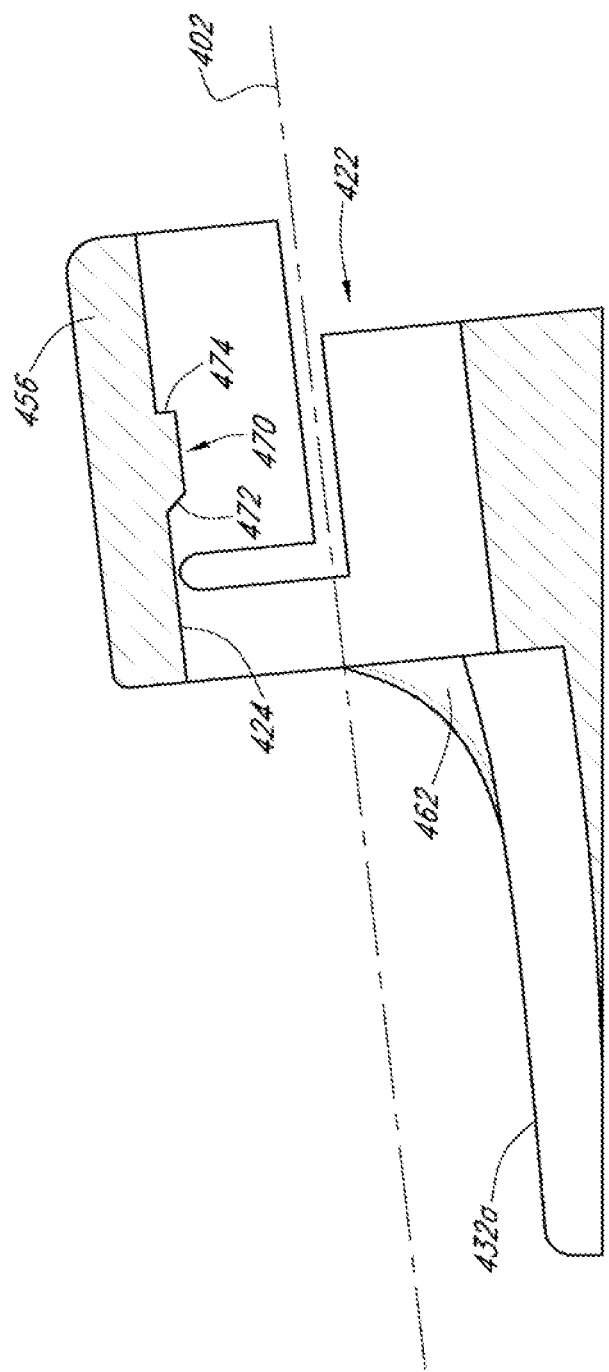
FIG. 40 is a cross-section of the retainer taken along line 40-40 in FIG. 33 without the anchor pad.
Figure 41:
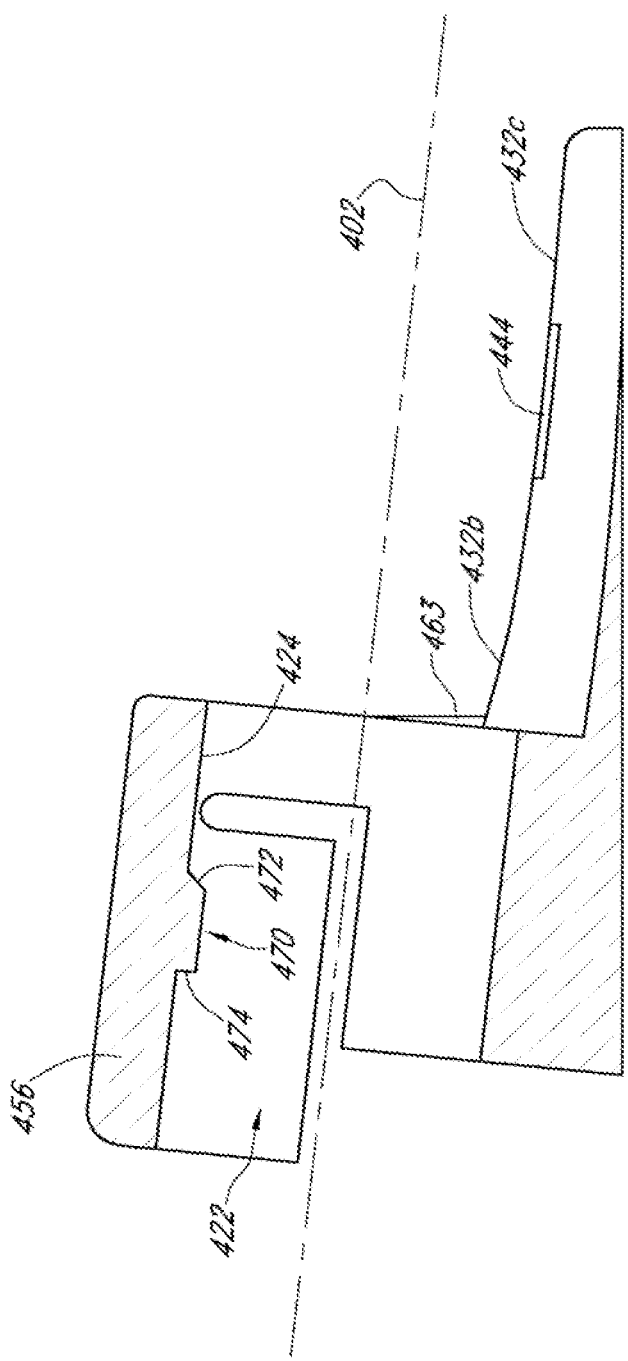
FIG. 41 is a cross-section of the retainer taken along line 41-41 in FIG. 33 without the anchor pad.

As can best be seen in FIGS. 40-41, the inner surface of flap 456 facing channel 422 may comprise at least one inwardly extending tang 470 configured to interact with an corresponding surface on the medical article to be retained, as will be discussed in greater detail below. Tang 470 has an asymmetrical shape to facilitate insertion and retention of medical articles such as medical article 20. In particular, it can be seen that the proximal face 472 of tang 470 is oriented at an angle which is substantially less than 90° to the interior surface 424 of channel 422. This shallow angle facilitates the insertion of the medical article 20 into the channel 422 from the proximal side of the channel, allowing the medical article 20 to be translated distally along the channel in a longitudinal direction without catching on the proximal face 472 of tang 470. The distal face 474 of tang 470 forms an angle which is close to or equal to 90° with the interior surface 424 of channel 422. This angle allows the distal face 474 of tang 470 to catch on a corresponding surface of the medical article to inhibit longitudinal movement of the medical article 20 in a proximal direction along the channel 422.

Figure 42:
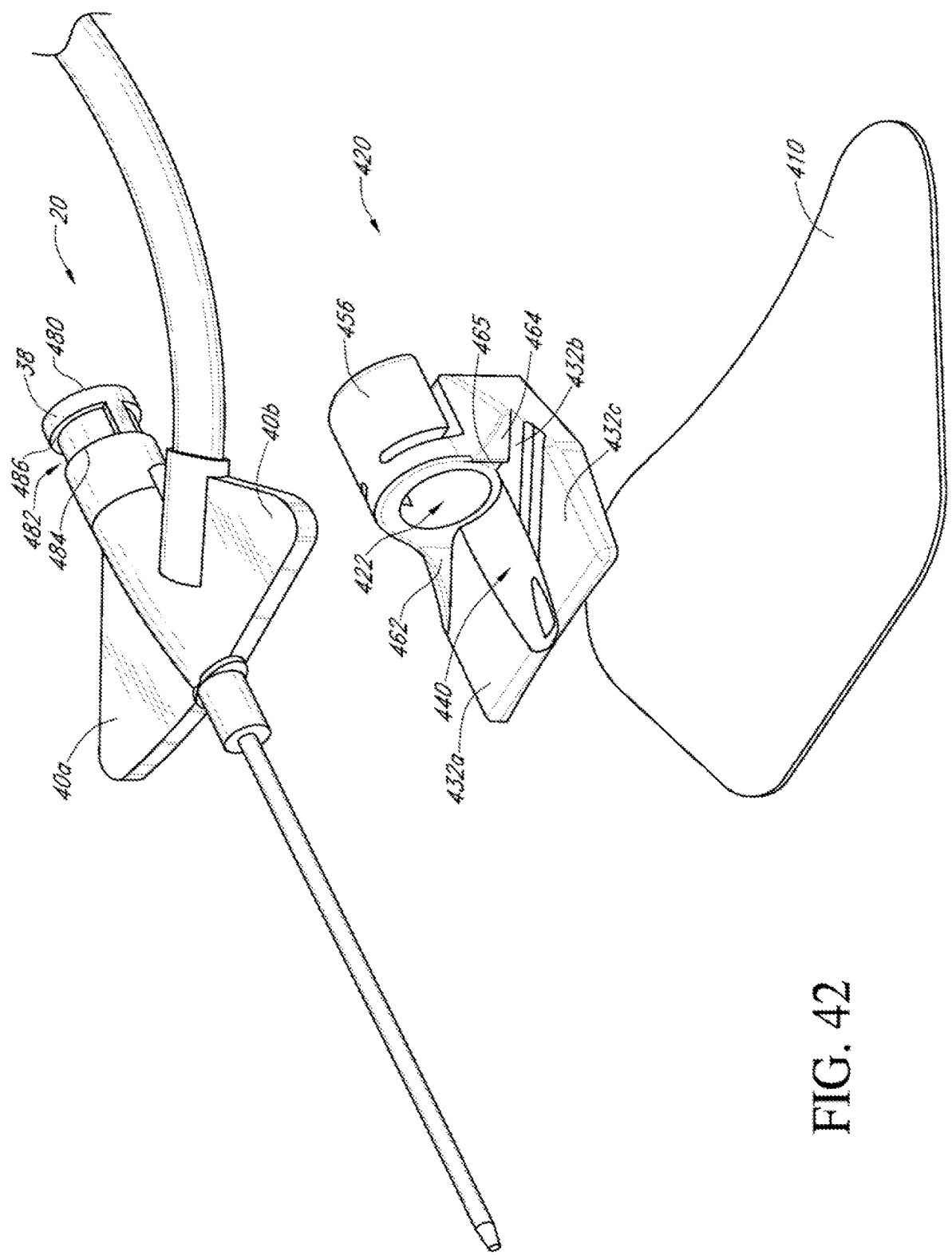
FIG. 42 is an exploded assembly view of the securement device and medical article of FIG. 31.
Figure 43:
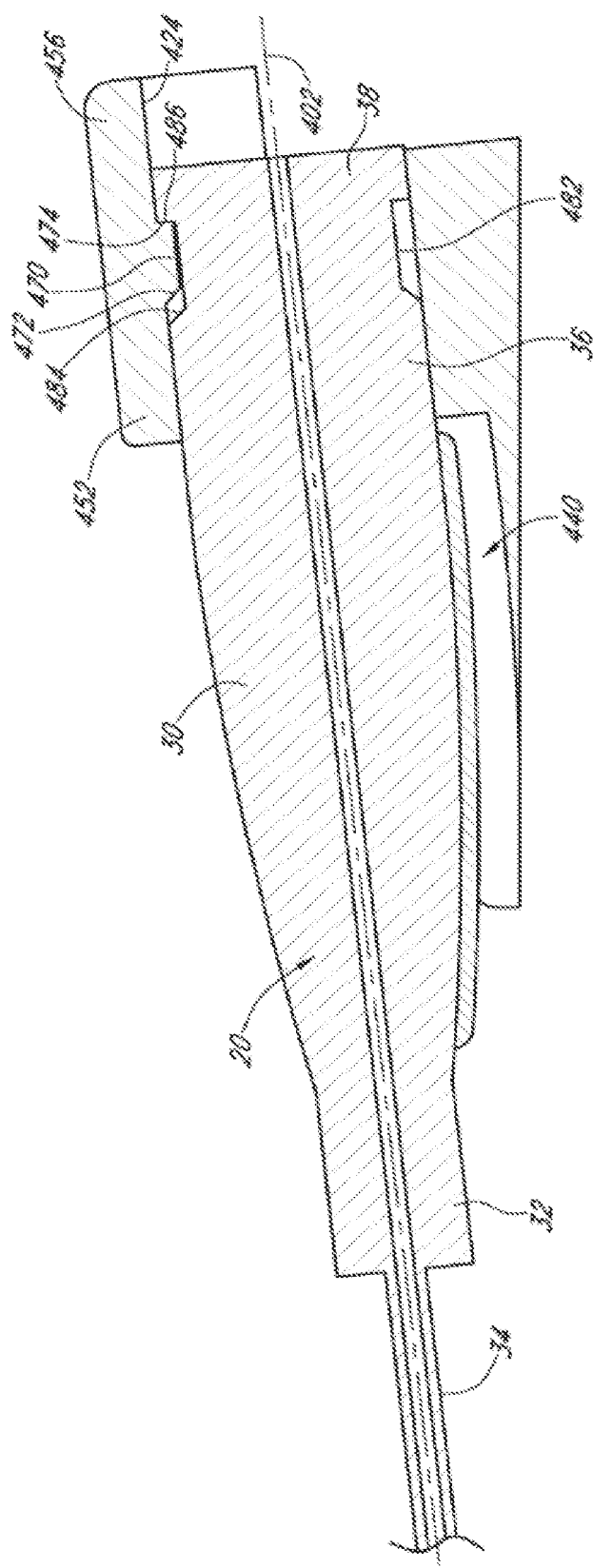
FIG. 43 is a side cross-section of the securement device and retained medical article of FIG. 32, taken along the longitudinal axis of the securement device and shows a tang of a biased flap engaged with a recess in the medical article.
Figure 44:
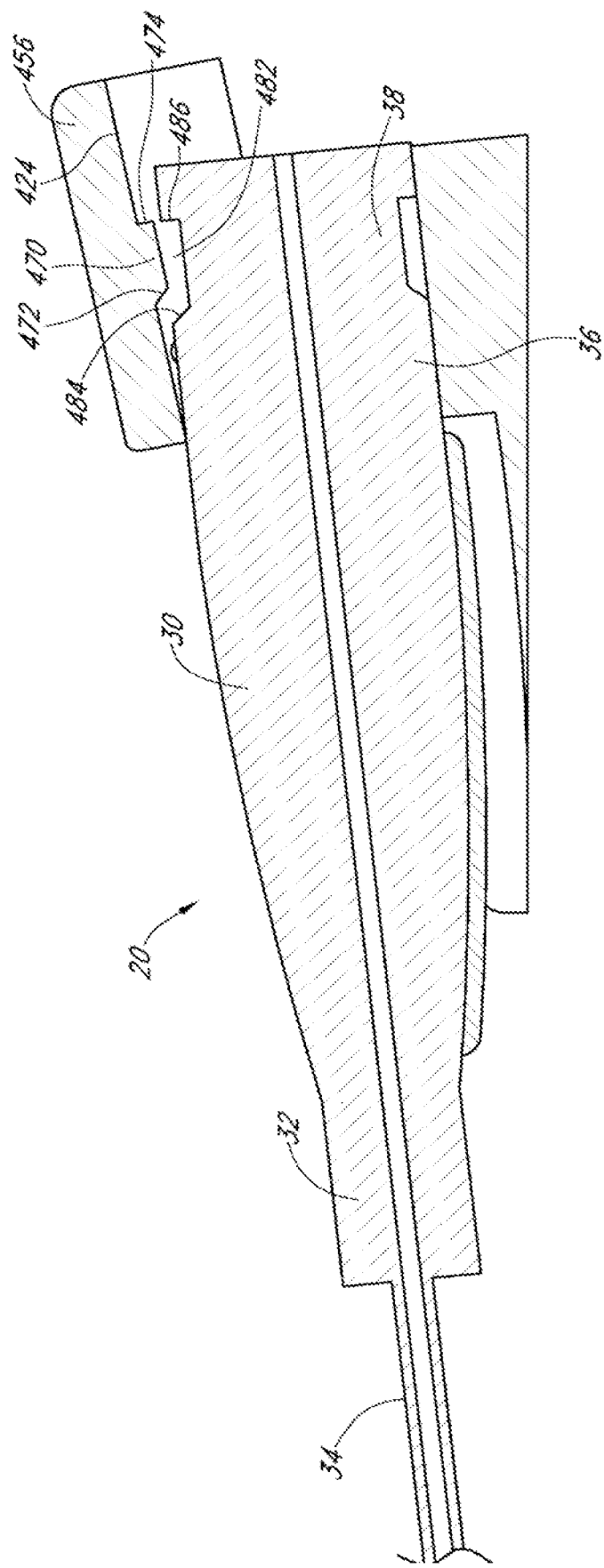
FIG. 44 is the same view as FIG. 43 except that the tang has been lifted away from the medical article to disengage the medical article from the retainer.

Operation of the securement system 400 is now described with respect to FIGS. 42-44. In certain embodiments, the tip 34 of medical article 20 may be inserted into the skin of the patient prior to securement of the medical article 20 within the securement device 400. The securement system 400, including the anchor pad 410 and the retainer 420, is aligned with the medical article 20 such that the distal end 36 of the medical article 20 is aligned with the proximal end of channel 422. The distal end 36 of the medical article 20 is then inserted into the channel 422 and translated longitudinally in a distal direction. The distal edge 480 of the medical article will initially contact the proximal face 472 of tang 470, which extends downwardly into the channel 422. Because the proximal face 472 is canted in a distal direction, pressure of the distal edge 480 on the proximal face 472 of tang 470 will cause the flap 456 to bend upward, away from the medical article, allowing passage of a portion of the medical article 20 through channel 422 past the tang 470.

As can be seen in FIG. 42, the connection means 38 of the medical article 20 comprise a depression, grove, or recess 482 extending radially inward and almost 180° about the upper surface of medical article 20. As can be seen in FIG. 43, the depression 482 has a longitudinal width which is greater than the longitudinal width of tang 470, and a depth which is greater to or substantially equal to the height of tang 470, such that when the medical article 20 is longitudinally translated such that the distal face 486 passes the distal face 474 of tang 470, the biased flap 456 can move downward against the upper surface of medical article 20 and the tang 470 can rest within depression 482 without the proximal face 472 of tang 470 contacting the proximal face 484 of depression 482. Longitudinal translation of the medical article 20 may continue until the distal edges of wings 40a and 40b of medical article 20 abut the proximal face 462 of footing 460a and the interior proximal face 465 of footing 460b, respectively.

Longitudinal translation of the medical article 20 in the distal direction is thus inhibited at least by abutment of the distal edges of the longitudinally extending wings 40a and 40b with proximal surfaces 462 and 465 of footings 460a and 460b. Longitudinal translation of the medical article 20 in the proximal direction will be inhibited by the abutment of distal face 474 of tang 470 against the distal face 486 of depression 482 in medical article 20, so long as the tang 470 is located within the depression. In contrast to proximal edge 472 of tang 470, which is canted to prevent the proximal edge from inhibiting movement of the medical article, the distal edge 474 is oriented at a substantially right angle to the interior surface 424 of channel 422, and will thus prevent movement of the medical article 20 in the proximal direction. In the illustrated embodiment, the tang 470 is located at a position along the length of the channel 422 such that longitudinal play of the medical article is reduced or substantially eliminated, to prevent the article 20 from sliding back and forth before contacting an abutment surface.

Transverse motion of the medical article 20 can be inhibited by the upper surface of channel 422, and in particular by cylindrical portion 452 of the retention structure 450. Rotation and lateral translation of the medical article can be inhibited by the sides of channel 422 as well as by the abutment of wings 40a and 40b against faces 462 and 465 of footings 460a and 460b.

As illustrated in FIG. 44, lifting of the flap 456 by a caregiver permits withdrawal of the medical device 20 from the channel 422, as the distal face 474 of tang 470 no longer abuts the distal face 486 of depression 482 in medical article 20. The caregiver may then grasp the distal edges of wings 40a and 40b to translate the medical article in a proximal direction and withdraw the medical article 20 from channel 422. Lifting of the flap 456 may be facilitated by the overhang of flap 456 in the distal direction beyond the distal end of the base of channel 422, or alternately by the sloped upper surface of footings 460a and 460b leading to the longitudinally extending grooves 458a and 458b.

The various embodiments of securement devices and techniques described above thus provide a number of ways to provide safe and releasable securement for medical articles to the skin of a patient. In addition, the techniques described may be broadly applied for use with a variety of medical lines and medical procedures.

Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and systems have been disclosed in the context of certain embodiments and examples, it will be understood by those skilled in the art that these techniques and systems may be extended beyond the specifically disclosed embodiments to other embodiments and/or uses and obvious modifications and equivalents thereof. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein disclosed should not be limited by the particular disclosed embodiments described above.

What is claimed is:

1. A securement kit, comprising:
 a catheter, comprising:
  a catheter shaft; and
  a hub in fluid communication with the catheter shaft, the hub comprising:
   a cylindrical body having a proximal end and a distal end; and
   a first wing and a second wing extending from the cylindrical body between the proximal end and the distal end; and
 a securement device, comprising:
  an anchor pad configured to be adhered to a patient; and
  a retainer coupled to the anchor pad, the retainer comprising:
   a front abutment surface including an open distal semi-cylindrical channel configured to receive the distal end of the cylindrical body of the hub, the open distal semi-cylindrical channel including opposing inwardly extending distal retention members;
   a rear abutment surface including an open proximal semi-cylindrical channel configured to receive the proximal end of the cylindrical body of the hub, the open proximal semi-cylindrical channel including opposing inwardly extending proximal retention members; and
   a laterally extending receiving space between the front abutment surface and the rear abutment surface configured to receive the first wing and the second wing, the laterally extending receiving space including a central channel connecting the open distal semi-cylindrical channel to the open proximal semi-cylindrical channel, the central channel configured to receive the cylindrical body of the hub, the central channel including an elliptical aperture configured to receive a lower surface of the cylindrical body of the hub therein, such that the cylindrical body of the hub directly contacts the anchor pad.

2. The securement kit according to claim 1, wherein the hub of the catheter further includes a tubular portion in fluid communication with the hub of the catheter and extending at an angle therefrom, and wherein the laterally extending receiving space includes a side channel extending from the central channel, the side channel configured to receive the tubular portion.

3. The securement kit according to claim 2, wherein the tubular portion extends through the second wing and is connected to an extension tube.

4. The securement kit according to claim 1, wherein the anchor pad has a generally trapezoidal shape narrowing in a distal direction and is symmetrical about a longitudinal axis of the retainer.

5. The securement kit according to claim 1, wherein the opposing inwardly extending proximal retention members and the opposing inwardly extending distal retention members comprise a resilient material.

6. The securement kit according to claim 1, wherein the opposing inwardly extending proximal retention members are separated by a distance less than a diameter of the proximal end of the cylindrical body of the hub.

7. The securement kit according to claim 1, wherein the opposing inwardly extending distal retention members are separated by a distance less than a diameter of the proximal end of the cylindrical body of the hub.

8. The securement kit according to claim 1, wherein a height of the front abutment surface is equal to a thickness of the first wing and the second wing.

9. The securement kit according to claim 8, wherein an upper surface of the laterally extending receiving space is substantially parallel to an upper surface of the front abutment surface.

* * * * *